United States Patent
McNair

(10) Patent No.: US 11,842,795 B1
(45) Date of Patent: Dec. 12, 2023

(54) IRRITABLE BOWEL SYNDROME DIAGNOSTIC SENSOR AND DECISION SUPPORT TOOL

(71) Applicant: CERNER INNOVATION, INC., Kansas City, KS (US)

(72) Inventor: Douglas S. McNair, Seattle, WA (US)

(73) Assignee: Cerner Innovation, Inc., Kansas City, MO (US)

(*) Notice: Subject to any disclaimer, the term of this patent is extended or adjusted under 35 U.S.C. 154(b) by 893 days.

(21) Appl. No.: 16/717,801

(22) Filed: Dec. 17, 2019

Related U.S. Application Data

(60) Provisional application No. 62/780,329, filed on Dec. 17, 2018.

(51) Int. Cl.
*G16B 40/00* (2019.01)
*G16H 50/20* (2018.01)
(Continued)

(52) U.S. Cl.
CPC .............. *G16B 40/00* (2019.02); *G16B 10/00* (2019.02); *G16B 30/00* (2019.02); *G16H 50/20* (2018.01)

(58) Field of Classification Search
CPC ........ G16B 40/00; G16B 10/00; G16B 30/00; G16H 50/20
(Continued)

(56) References Cited

U.S. PATENT DOCUMENTS 8,478,544 B2   7/2013   Colwell et al.
9,663,831 B2   5/2017   Apte et al.
(Continued)

FOREIGN PATENT DOCUMENTS

EP         3262215 A1      1/2018
WO   WO-2011053831 A1 *   5/2011   .......... C12Q 1/6827
(Continued)

OTHER PUBLICATIONS

Engelhart et al., "Disease Associations with Isolated Elevations of each of the four IgG Subclasses", Seminars in Arthritis and Rheumatism, vol. 47, No. 2, 2017, pp. 276-280.
Iamed, Khaled H., "Trend Detection in Hydrologic Data: The Mann-Kendall Trend Test Under the Scaling Hypothesis", Journal of Hydrology, vol. 349, No. 3-4, 2008, pp. 350-363.
Hussain et al., "Significantly Increased IgG2 Subclass Antibody Levels to Blastocystis Hominis in Patients with Irritable Bowel Syndrome", The American Society of Tropical Medicine and Hygiene, vol. 56, No. 3, Mar. 1997, pp. 301-306.
(Continued)

*Primary Examiner* — Michael Tomaszewski
(74) *Attorney, Agent, or Firm* — Invoke

(57) ABSTRACT

An improved decision support tool is provided for detecting (or for diagnosing or treating human patient at risk for developing) a functional gastrointestinal condition, such as irritable bowel syndrome (IBS). The decision support tool, which may comprise a smart sensor, determines microbiota diversity, relative abundances of microbial taxa, trends in the relative abundances, and concentrations of immunoglobulin G subclasses, from specimens from the subject, and combines these determined values using a classifier to automatically ascertain whether changes or trends in the values are statistically significant and clinically actionable with respect to diagnosing and managing the subject's condition. The decision support tool may further initiate an intervening action based on this determined joint significance, such as generating an electronic notification, modifying a treatment program, providing a recommendation, automatically allocating health care resources to the patient, or automatically scheduling a consultation with a caregiver.

22 Claims, 10 Drawing Sheets

(51) Int. Cl.
  *G16B 10/00* (2019.01)
  *G16B 30/00* (2019.01)
(58) Field of Classification Search
  USPC .......................................... 705/2–3; 702/19
  See application file for complete search history.

(56) References Cited

U.S. PATENT DOCUMENTS

| | | | |
|---|---|---|---|
| 9,703,929 B2 * | 7/2017 | Apte .................... | G16B 50/00 |
| 9,719,144 B2 | 8/2017 | Krajmalnik-Brown et al. | |
| 9,739,786 B2 | 8/2017 | Westin et al. | |
| 9,758,839 B2 | 9/2017 | Apte et al. | |
| 9,760,676 B2 | 9/2017 | Apte et al. | |
| 10,668,118 B2 | 6/2020 | Lynch et al. | |
| 10,954,571 B2 | 3/2021 | Mougeot et al. | |
| 2008/0166719 A1 * | 7/2008 | Lois ................... | G01N 33/6869 |
| | | | 435/7.1 |
| 2010/0094560 A1 * | 4/2010 | Lois .................... | G01N 33/564 |
| | | | 702/179 |
| 2016/0120915 A1 | 5/2016 | Blaser et al. | |
| 2016/0263166 A1 | 9/2016 | Elinav et al. | |
| 2017/0067107 A1 * | 3/2017 | Sandrin ................ | C12Q 1/6883 |
| 2017/0286620 A1 | 10/2017 | Apte et al. | |
| 2018/0010164 A1 | 1/2018 | Taneja | |
| 2020/0399673 A1 * | 12/2020 | Kashyap ................ | C04B 28/02 |

FOREIGN PATENT DOCUMENTS

| | | | |
|---|---|---|---|
| WO | 2013/012332 A1 | 1/2013 | |
| WO | WO-2014188378 A1 * | 11/2014 | ........... C07D 495/04 |

OTHER PUBLICATIONS

Floch et al., "The Microbiota in Gastrointestinal Pathophysiology: Implications for Human Health, Prebiotics, Probiotics, and Dysbiosis", Academic Press, 2016, 442 pages.

Izard et al., "Metagenomics for Microbiology", Academic Press, 2014, 188 pages.

Notice of Allowance received for U.S. Appl. No. 16/707,786, dated Jun. 23, 2022, 9 pages.

\* cited by examiner

| | TAX_NAME | TAX_RANK | COUNT | COUNT_NOR | TAXON | PARENT |
|---|---|---|---|---|---|---|
| 1 | ROOT | ROOT | 71114 | 1000000 | 1 | 0 |
| 2 | BACTERIA | SUPERKING | 71114 | 1000000 | 2 | 131567 |
| 3 | BACTEROIDACEAE | FAMILY | 16605 | 233498 | 815 | 171549 |
| 4 | BACTEROIDES | GENUS | 16600 | 233428 | 816 | 815 |
| 5 | BACTEROIDES THETAIOTAOMICRON | SPECIES | 11 | 154 | 818 | 816 |
| 6 | BACTEROIDES UNIFORMIS | SPECIES | 91 | 1279 | 820 | 816 |
| 7 | BACTEROIDES VULGATUS | SPECIES | 11493 | 161613 | 821 | 816 |
| 8 | PARABACTEROIDES DISTASONIS | SPECIES | 1146 | 16114 | 823 | 375288 |
| 9 | ROSEBURIA | GENUS | 5112 | 71884 | 841 | 186803 |
| 10 | FAECALIBACTERIUM PRAUSNITZII | SPECIES | 4617 | 64923 | 853 | 216851 |
| 11 | DESULFOVIBRIO | GENUS | 2 | 28 | 872 | 194924 |
| 12 | DESULFOVIBRIO SP. | SPECIES | 2 | 28 | 885 | 872 |
| 13 | HERBASPIRILLUM | GENUS | 10 | 140 | 963 | 75682 |
| 14 | HERBASPIRILLUM SEROPEDICAE | SPECIES | 10 | 140 | 964 | 963 |
| 15 | BACTEROIDETES | PHYLUM | 21020 | 295581 | 976 | 68336 |
| 16 | PROTEOBACTERIA | PHYLUM | 2467 | 34690 | 1224 | 2 |
| 17 | FIRMICUTES | PHYLUM | 45069 | 633757 | 1239 | 2 |
| 18 | SARCINA | GENUS | 781 | 10982 | 1266 | 31979 |
| 19 | STREPTOCOCCACEAE | FAMILY | 957 | 13457 | 1300 | 186826 |
| 20 | STREPTOCOCCUS | GENUS | 930 | 13077 | 1301 | 1300 |
| 21 | STREPTOCOCCUS THERMOPHILUS | SPECIES | 877 | 12332 | 1308 | 1301 |
| 22 | LACTOCOCCUS | GENUS | 5 | 70 | 1357 | 1300 |
| 23 | BACILLALES | ORDER | 2 | 28 | 1385 | 91061 |
| 24 | CLOSTRIDIUM | GENUS | 658 | 9252 | 1485 | 31979 |
| 25 | LACTOBACILLUS | GENUS | 38 | 534 | 1578 | 33958 |
| 26 | LACTOBACILLUS DELBRUECKII | SPECIES | 9 | 126 | 1584 | 1578 |
| 27 | CORYNEBACTERIACEAE | FAMILY | 3 | 42 | 1653 | 85007 |
| 28 | BIFIDOBACTERIUM | GENUS | 3 | 42 | 1678 | 31953 |

~200 TO ~500 MORE ROWS IN TABLE

*FIG. 4.*

| Patient... | enter |
|---|---|
| Harmonic mean of Firmicutes:Bacteroidetes ratio | 1.82 |
| Arithmetic mean of Shannon diversity index | 2.56 |
| Serum IgG2 proportion of total IgG | 0.263 |

| evaluate | results |
|---|---|
| data complete? | Yes |
| Likelihood of IBS-D or IBS-M responsive to eluxadoline, alosetron, or rifaximin is... | Low  2% |

FIG. 5A.

| Patient... | enter |
|---|---|
| Harmonic mean of Firmicutes:Bacteroidetes ratio | 1.82 |
| Arithmetic mean of Shannon diversity index | 2.56 |
| Serum IgG2 proportion of total IgG | 0.600 |

| evaluate | results |
|---|---|
| data complete? | Yes |
| Likelihood of IBS-D or IBS-M responsive to eluxadoline, alosetron, or rifaximin is... | Very High  75% |

FIG. 5B.

```
###########################################################

#   IgG subclasses association with IBS

##################################################### library(vegan)
library(GUniFrac)

# load data
dat <- read.csv(file="c:/0_cerdsm/IP/irritable_bowel_IgG_microbiome/dsm_IgG_frac.csv", header=TRUE,
        colClasses=c("character","factor",rep("numeric", 4)))
# ID, group, IgG1, IgG2, IgG3, IgG4 as fractions
#   0=normal
#   1=IBS
dat <- dat[, -1]

# logistic regression of IBS group on IgG2 concentration as fraction of IgG total concentration
fit2 <- glm(group ~ IgG2 , family=binomial, data=dat)  # ******
summary(fit2)
# Coefficients:
Estimate Std. Error z value Pr(>|z|)
# (Intercept)  -3.361    1.237   -2.718  0.00657 **
# IgG2         11.059    3.967    2.788  0.00530 **
```

FIG. 7A.

```
###############################################################

#  Diagnostic/prognostic logistic regression model of IBS-D and IBS-M

######################################################### library(vegan)
library(GUniFrac)

dat <- read.csv(file="c:/0_cerdsm/IP/irritable_bowel_IgG_microbiome/dsm_IBS_cohort.csv", header=TRUE,
        colClasses=c("character", "factor", rep("numeric",3)))
#              ID, group, hmean.FB, dv, IgG2
dat <- dat[,-1]

# transform alpha diversity to gamma diversity and create derived variable with Firmicutes:Bacteroidetes ratio
harmonic mean
dat$X <- dat$hmean.FB/dat$dv ctrl <- glm.control(epsilon = 1e-6, maxit = 50, trace = FALSE)
fit <- glm(group ~ X + IgG2, family=binomial, data=dat)
summary(fit)
# Coefficients:
Estimate Std. Error z value Pr(>|z|)
# (Intercept) -9.0669    3.2979  -2.749  0.00597 **
# X            1.4951    0.5605   2.667  0.00765 **
# IgG2        15.2072    6.8684   2.214  0.02682 *
```

FIG. 7B.

```
###########################################################

#   Generate receiver operating characteristic (ROC) curve of IBS prediction

##################################################### library(pROC)

load data
ds4 <- read.csv(file="c:/0_cerdsm/IP/irritable_bowel_IgG_microbiome/ibs_roc.csv")
roc1 <- roc(ds4[,1] ~ ds4[,2], percent=TRUE,
# arguments for auc
# partial.auc=c(100, 90), partial.auc.correct=TRUE,
# partial.auc.focus="sens",
# arguments for ci
  ci=TRUE, boot.n=100, ci.alpha=0.9, stratified=FALSE,
# arguments for plot
# auc.polygon=TRUE, max.auc.polygon=TRUE,
  plot=TRUE, grid=TRUE, print.auc=TRUE, show.thres=TRUE)
sens.ci <- ci.se(roc1, specificities=seq(0, 100, 5))
plot(sens.ci, type="shape", col="lightblue")
plot(sens.ci, type="bars")

roc(ds4[,1] ~ ds4[,2], ds4, plot=TRUE, col="red")

# column-major
dsm <- matrix(c(17,2,4,17), ncol=2)
fisher.test(dsm)
```

FIG. 7C.

IRRITABLE BOWEL SYNDROME DIAGNOSTIC SENSOR AND DECISION SUPPORT TOOL

CROSS-REFERENCE TO RELATED APPLICATIONS

This application claims the benefit of U.S. Provisional Application No. 62/780,329, titled "IRRITABLE BOWEL SYNDROME DIAGNOSTIC SENSOR AND DECISION SUPPORT TOOL," filed Dec. 17, 2018, which is hereby expressly incorporated by referenced in its entirety.

BACKGROUND

The human body is host to a complex and abundant aggregation of microbes, collectively referred to as the microbiota. Anatomical sites that are the subject of measurements of microbiota include gut, skin, genitals, oropharynx, and respiratory tract. Microbiota in body fluids such as blood, urine, and sputum are also routinely measured. The relevance of such measurements to medical diagnostics and therapeutics is diverse. By way of example, the gut microbiota has physiological functions associated with nutrition, the immune system, and defense of the host. The intestinal microbiota plays a number of important roles in mammalian health, including gut development, extraction of energy from food, protection against pathogens, and development, maturation, and responsiveness of the immune system. Alterations in the composition of the intestinal bacterial communities have been implicated in obesity, inflammatory bowel disease, diabetes, and a variety of disease states.

For instance, Irritable Bowel Syndrome (IBS) is a chronic, relapsing functional gastrointestinal condition that affects approximately 11% to 15% of the global population. In recent years the incidence and prevalence of IBS continue to increase. IBS has significant economic impact in terms of absenteeism among working-age persons and in terms of health services spending. Features of IBS include abdominal pain and bloating, diarrhea or constipation or alternation between these, entailing a negative impact on quality of life and interfering with social interactions including employment. However, to date, the conventional technology and approaches to healthcare decision support have not understood or effectively utilized the range of gut microbiota compositional states during health in efforts to define and characterize prognosis, progression of illness, and treatment effectiveness for patients suffering from IBS.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

Technologies described herein provide an improved decision support tool for diagnosing and managing, including treating or modifying care provided to human patients having or at risk for developing a functional gastrointestinal condition, such as irritable bowel syndrome (IBS). At a high level, embodiments of the technology described herein may (1) determine microbiota diversity, relative abundances of microbial taxa, and trends in the relative abundances in specimens collected serially from a mammalian subject; (2) and further may combine this with measurements of one or more immunoglobulin G subclasses to automatically ascertain whether the patterns are statistically significant and clinically actionable with respect to diagnosing and managing a functional gastrointestinal condition, such as IBS; and (3) if so, automatically initiate an intervening action, such as issuing a notification or alert, scheduling healthcare resources, or generating or modifying a care plan for the patient, or generating decision support recommendations, which may include statistically robust quantitative interpretations of the patterns or pattern changes. In some embodiments, patterns of operational taxonomic units' (OTUs') relative abundances or diversity are determined and monitored or analyzed to automatically ascertain quantitatively whether statistically significant alterations or trends are exhibited that in combination with alteration in relative concentration of one or more immunoglobulin G (IgG) subclasses are noteworthy or merit decision-making and action in regard to diagnosing and managing a functional gastrointestinal condition, such as IBS.

In particular, one aspect of the technologies described herein comprises a decision support tool which may include or utilize an improved smart sensor system that detects or characterizes IBS or a similar functional gastrointestinal conditions. In some embodiments, smart sensor utilizes endotypes of functional gastrointestinal conditions, such as IBS, which may be detected and characterized in terms of a joint machine-learning classifier model that combines determinations of fecal microbiota profiles at the 'phylum' taxonomic level, alpha diversity at the 'genera' taxonomic level, and serum immunoglobulin G subclass profiles. Where clinical significance of the resulting classification is determined, an intervening action is initiated. In this way, embodiment described herein provide improved clinical decision support tools for preventive, diagnostic, and therapeutic applications of medicine. In particular, emerging health conditions, which may include deterioration, sickness, health risks, disease, or altercation, for example, may be identified sooner or in a less invasive manner Thus, by employing the techniques described herein, embodiments can overcome the deficiencies that are associated with the conventional industry practice.

BRIEF DESCRIPTION OF THE DRAWINGS

The present invention is described in detail below with reference to the attached drawing figures, wherein:

FIG. 4 depicts example results from 16S rRNA pyrosequencing, according to the process of FIG. 3;

FIGS. 5A and 5B depict example graphical user interfaces of an embodiment of a decision support tool for diagnosing and managing IBS and applying the method of FIG. 2, in accordance with an embodiment of the disclosure;

FIGS. 7A-7C illustratively provide an example embodiment of a computer program routine for implementing aspects of a decision support tool that utilizes the method of FIG. 2, in accordance with an embodiment of the disclosure.

DETAILED DESCRIPTION

Figure 1A:
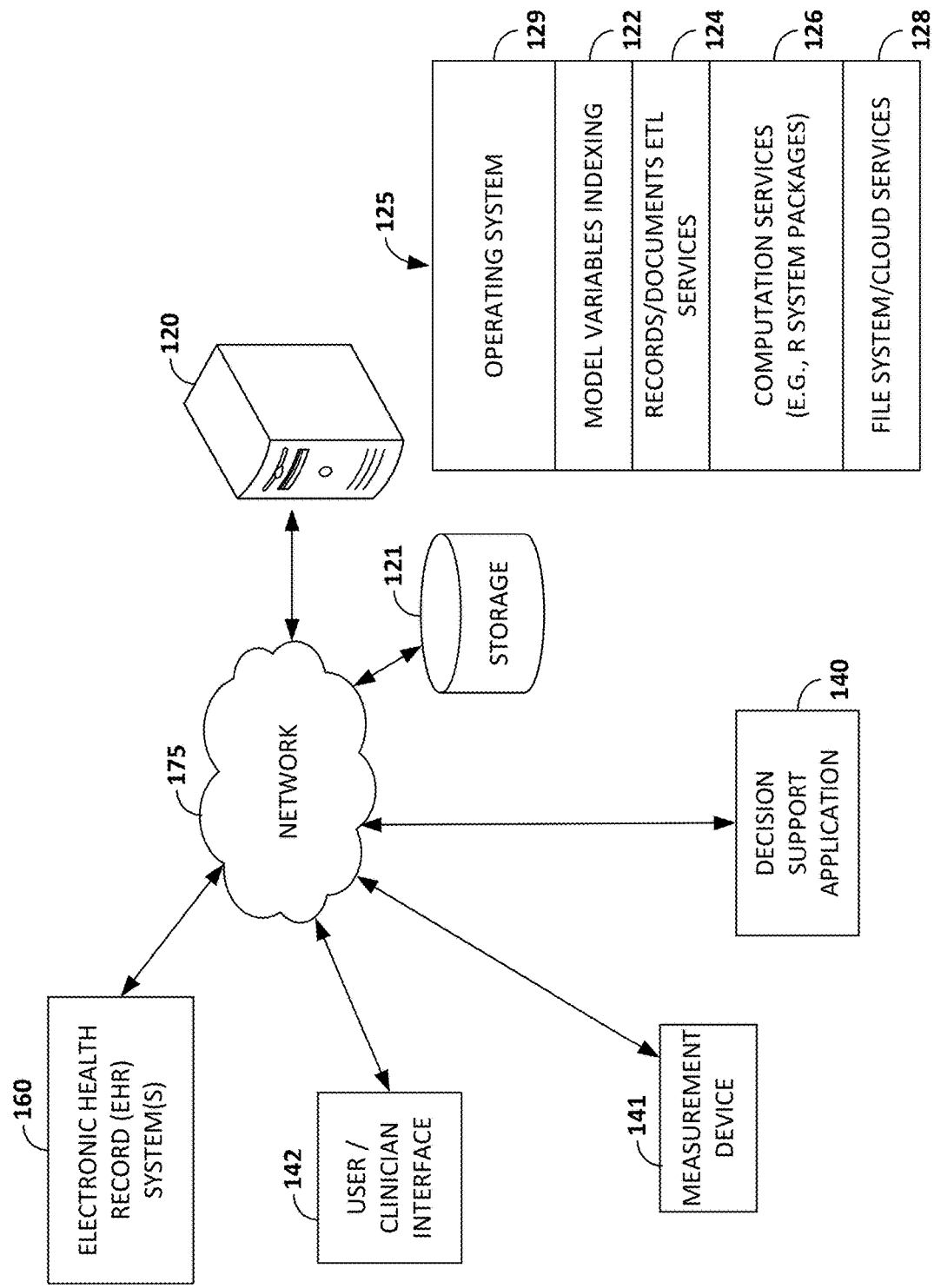
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media, which is described herein. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

At a high level, this disclosure describes, among other things, technologies for an improved decision support tool for detecting (and treating human patients based on) changes or trends in microbiota-related activity of the patient.

Technologies described herein provide an improved decision support tool for diagnosing and managing, including treating or modifying care provided to human patients having or at risk for developing a functional gastrointestinal condition, such as irritable bowel syndrome (IBS). Embodiments of the decision support tool may comprise a smart sensor that detects or senses statistically significant alterations such as changes or trends in the microbiota-related relative abundances and diversity in combination with alteration in relative concentration of one or more immunoglobulin G (IgG) subclasses. In particular, some embodiments of the smart sensor (or decision support tool) are configured to utilize endotypes of functional gastrointestinal conditions, such as IBS, which are detected and characterized in terms of a joint machine-learning classifier model. The joint classifier model may combine determinations of fecal microbiota profiles at the 'phylum' taxonomic level, alpha diversity at the 'genera' taxonomic level, and serum immunoglobulin G subclass profiles. Where clinical significance of the resulting classification is determined, an intervening action is initiated, such as by way of example and without limitation, generating an electronic notification and providing the electronic notification to the patient or caregiver, modifying a treatment program, providing a recommendation, automatically allocating health care resources to the patient, or automatically scheduling a consultation with a caregiver. In some embodiments, the electronic notification may further include statistically robust quantitative interpretations of the patterns or pattern changes. In some embodiments, the decision support tool comprises (or may be embodied as) a smart sensor system that senses or receives serial of microbiota data (or successive measurements of microbiota data) about a human patient and detects the changes or trends of microbiota activity and the changes in relative concentration of an IgG subclass. In some embodiments, smart sensor uses the machine learning classification, such as described herein, for detecting or responding to the clinically significant changes or trends.

According to one aspect and as further described herein, serial or successive specimens are acquired from an anatomical site (such as genitals or skin or pharynx) or specimen type (such as feces or blood or sputum) of a subject, such as a human patient or animal. From these specimens, abundances of microbial and/or taxa are measured, and from the serial or successive samples, a time series is formed. In an embodiment, 16S rRNA sequencing methods are utilized, which may include amplification, depending on the total count of organisms in the specimens and the efficiency of nucleotide extraction. In some embodiments, genera counts with phylum-level mappings are determined, which provide advantages, as explained herein.

Approximately contemporaneously (or within a similar time interval of each of the microbiota specimen collections) serum specimens of immunoglobulin G are also acquired form the subject. For each serum specimen, IgG2 subclass concentration is determined and expressed as a fraction of total serum IgG, thereby forming an IgG time series. Some embodiments may begin by determining or receiving measurement data from the microbiota-related and serum specimens. The determined taxa abundance data and IgG2 subclass concentration data may be stored until enough samples are acquired to comprise time series of sufficient length, which may be predetermined or based on a particular condition of the subject, a treatment, as described herein.

In some embodiments, the specimens may be associated with a diagnostic health condition of interest in the subject sampled, such as IBS, with one or more taxa pertinent to management of the health condition, and with the subject's treatment metadata (or condition metadata) corresponding to the collection date on which each specimen was acquired.

After accumulating enough measurement data to determine a time series of sufficient length, then the taxa may be filtered or truncated, to retain genera-level taxa having abundance greater than a threshold value, such as 0.05%, according to one example embodiment actually reduced to practice and described herein, and the phylum-level membership information for each retained genus OTU.

Next, rarefaction may be performed on each sample's taxa abundances thereby normalizing counts to a standard count. In some embodiments, such as in the case of in the case of fecal microbiota time series, N may be approximately 10,000.

The alpha diversity of the bacterial taxa of each member of the time series is determined, and the mean alpha diversity is determined. In one embodiment, the alpha diversity (for example, Shannon, Simpson, or Chao) may be determined for each time series member. The mean alpha diversity may be determined as the arithmetic mean of the diversity values of the microbiota-related time series measurements. Additionally, in some embodiments, the rarefied relative abundances of genera in the phylum Firmicutes are totalized and the rarefied relative abundances of genera in the phylum Bacteroidetes are totalized in each of the time series of measurement specimens.

Determine the Firmicutes to Bacteroidetes ratio (F/B ratio) for each member of the time series of measurement specimens, and further determine the harmonic mean of the determined F/B ratios. Determine the concentrations of total IgG and of IgG subclass 2 (IgG2). In particular, some embodiments determine the relative concentration of immunoglobulin G (IgG) subclasses in the serum specimen measurements.

Next, a classification model is determined and applied. In some embodiments, the classification model is determined to utilize the determined arithmetic mean of the diversity values the harmonic mean of the F/B ratio, and the ratio of IgG2 to IgG to determine the presence of statistically significant microbiota change and IgG2 subclass relative concentration change to the diagnosis or response treatment of the health condition of interest. In this way, the joint evidence from these determinations is combined to further ascertain the likely effectiveness of a medical treatment that is directed to microbiota profile, microbiota diversity, or immune response in the subject. The probability results from the classification model may be compared against a threshold for statistical significance. Where the classification model determines statistical significance (e.g., joint statistical significance is determined), then the decision support tool may initiate a decision support action, such as an intervening action, as described herein.

In this way, embodiments described herein facilitate improved decision support such as prognosis, progression of illness, or treatment effectiveness, for patient conditions that cause alterations in the composition of the intestinal bacterial communities, such IBS. This means that the practical applications of the embodiments described herein lead to a significant impact in clinical support systems and the healthcare industry in general. One practical application of these embodiments means that the decision support system is able to take a greater active role in monitoring the care of the patient.

As described above, IBS is a chronic, relapsing functional gastrointestinal condition that affects approximately 11% to 15% of the global population, and incidence and prevalence of IBS continues to increase. Differentiating between inflammatory bowel disease (IBD), such as Crohn's disease and ulcerative colitis, and non-inflammatory diarrhea, such as IBS, constitutes a major unmet need insofar as the causative biology and the treatments of each are widely different. Although the incidence and prevalence of IBS are increasing globally, the precise etiology remains unclear. Medical management of IBS is complex, costly, and has variable effectiveness, such that the medication regimen must be adjusted in a personalized fashion so as to discover which medications can modify the course of the disease for each individual. Some medications for IBS are expensive (for instance, the average wholesale price may exceed 1,300 per month of treatment), such that prompt, reliable, evidence-based determination of effective IBS prognosis, monitoring, determination of treatment regimen effectiveness and/or modification of treatment regimen(s)—such as provided by some embodiments of the decision support tool described herein—is highly desirable and would be clinically and financially preferable to the conventional technologies and the trial-and-error based approaches.

The most accepted hypothesis of IBS etiology is that complex interactions between gut microbiota, diet, sedentary lifestyle, neuropsychiatric comorbidities, genetics, environmental factors, and the host immune system lead to aberrant immune responses and hypersensitivity reactions with altered colonic transit times—decreased in the case of diarrhea-predominant IBS (IBS-D), and increased in the case of constipation-predominant IBS (IBS-C). Recent advances in next-generation sequencing technology have identified alteration of the composition and function of the gut microbiota, which is referred to as dysbiosis, in IBS. Severe IBS can cause a dramatic dysbiosis of gut microbiota; derangements of gut microbiota profiles in moderate or mild IBS can be subtle. Changes in host-microbiota interactions in IBS produce dysbioses in which microbiota are less diverse than in healthy persons, or in persons with IBS that is well-controlled. Furthermore, a trend of enriched beneficial bacteria and diminished opportunistic pathogen bacteria may serve as prognostic microbiome biomarkers of IBS severity and remission. Yet further, certain elements of therapeutics in IBS are directed to modulating the microbiota to achieve and sustain a microbiome composition having greater diversity of microbial taxa than the microbiome in basal untreated or under-treated conditions. However, none of the conventional technologies based on microbiota-related detection have adequate statistical sensitivity and specificity to afford reliable use in clinical diagnosis and management of IBS, which are achieved by the embodiments of the technologies described herein.

Additionally, the conventional technologies have a number of limitations and problems that are overcome by embodiments of the decision support tool or smart sensor technologies described herein. For instance, (1) conventional technologies for measurement and analytics emphasize single-specimen determination of microbiota present in a single sampled body site in a patient and thus do not even provide means for quantitative interpretation of microbiota changes, if any, between members of a succession of specimens serially collected from a body site from the patient over a period of time. Additionally, (2) the underlying methods of these technologies are qualitative and typically yield information consisting of graphical displays or descriptive statistics only, which do not reliably direct actions or quantitative interpretations. Furthermore, (3) the methods and equipment utilized by the conventional technologies is complex and not as amenable to automated, cost-efficacious, repeated and ongoing performance.

Additionally, (4) the conventional technologies lack adequate statistical sensitivity to ascertain health condition-related microbiota biomarker indices of exacerbation, remission, and treatment efficacy or non-efficacy, and, therefore, suffer from excessively high false-negative determinations, giving false reassurance regarding the presence or absence of the health condition or regression treatment efficacy. Similarly, (5) the conventional technologies have inadequate statistical specificity to rule-out conditions having health condition-related microbiota biomarker indices of exacerbation, remission, and treatment efficacy or non-efficacy. These conventional technologies therefore suffer from excessively high false-positive determinations of changes in diversity, health condition-related microbial taxa abundances, or relative-abundance profiles.

These and other deficiencies and limitations of the conventional technologies are mitigated or overcome by the improved technologies described herein. For instance, as described above, embodiments of the decision support tool described herein improve upon conventional sensors and technologies for detecting, ascertaining or treating patients based on, changes or trends in microbiota-related activity. Some of these improvements realized include that the embodiments described herein are not susceptible to biases, are more tolerant, such as tolerant of variable total bacteria count and relative OTU abundances from specimen to specimen, and provide the adequate statistical sensitivity and specificity to afford reliable use in clinical diagnosis and management of IBS. Additionally some embodiments of our decision support tool can further take advantage of IgG subclass indicia of host immune system responses to antigen exposures.

In contrast to research regarding the association of elevated IgG2 levels with IBS, which has been sparse with provisional results reflecting small-cohort experience of single institutions and uncontrolled observational studies, embodiments of the technologies described herein were derived in from analyses of a cohort of historical IBS-D or IBS-M patients (352,377 distinct IBS patients, who were diagnosed with ICD-10 K58.0, K58.2, or K58.8 or ICD-9 564.1 codes) in Cerner Health Facts® data warehouse, an electronic health record (EHR) derived de-identified HIPAA-compliant secondary-use-assented repository. The IBS-D and IBS-M cases were incident upon more than 820 U.S. health care institutions and affiliated ambulatory clinics and physician offices and spanning the 2000 through 2017 time period and containing the health records of more than 100,000,000 distinct patients, complete with longitudinal record linkage of their ongoing episodes of care. Unrelated to the IBS condition, a subset of 806 of these IBS patients had, for various reasons, had total IgG level and contemporaneous full IgG subclass concentrations measured in the course of their diagnostic work-ups or treatment of other comorbid conditions and, in some cases, multiple IgG subclass measurements had been made serially during the courses of the patients' treatment.

The balance of Health Facts® data warehouse contained a total of 81,268 distinct patients who did not have any GI condition but in whom total IgG level and contemporaneous full IgG subclass concentrations had been measured for other reasons. With these controls and the aforementioned IBS cases, the inventor and colleagues were able to discover and establish a definite association between IgG2 and symptomatic IBS, statistically-significant at $p<0.001$.

However, this alone is not sufficient for utilization by a decision support tool or smart sensor, such as the embodiments described herein, because absolute immunoglobulin levels vary widely as a function of age, health status, nutrition, infectious disease exposures, and other factors. To mitigate the effect of such variations in absolute immunoglobulin levels, embodiments of the technologies described herein derive a new and non-naturally occurring variable for utilization by the decision support tool (or smart sensor). (In some embodiments other determined variables or values (such as those relating to microbiota diversity and/or F/B-related determinations are also utilized.) In particular, to mitigate this effect, some embodiments determines the relative level of IgG2 as a fraction of the total IgG concentration. This procedure additionally serves to mitigate the biases that may arise due to different standard materials used in different laboratories for calibrating nephelometric and turbidimetric assays for the IgG subclasses. For instance, ordinarily the IgG2 in healthy adults comprises a fraction between 0.19 and about 0.30 of the serum total IgG. However, in symptomatic adult IBS patients, the inventor and his colleagues have discovered that IgG2 frequently constitutes a much higher fraction of total IgG in serum, typically between 0.30 and 0.50. Accordingly these discoveries are utilized as biomarkers by some embodiments described herein, for smart sensor (or monitoring) applications that provide caregivers improved detection and decision support for patients having IBS.

Moreover, previous studies on IBS, mostly based on fecal samples, suggest alterations in the intestinal microbiota. However, no consensus has been reached regarding the association between specific bacteria and IBS. The inventor and his colleagues explored the alterations of intestinal bacterial communities in IBS using sequencing of amplified 16S rRNA. Strong inter-individual variation was discovered in the composition of the bacterial communities in both patients and controls. These communities showed less diversity in IBS cases. Given the complex spectrum of GI microbiota, however, monitoring perturbations in selected species may not be not a useful indicator of IBS diagnosis nor of IBS treatment effectiveness due to a number of issues. Accordingly, some embodiments of the technologies described herein overcome these problems by deriving and utilizing for detection and monitoring, non-naturally occurring values comprising derangements in ratios of abundances at the phylum level, which also provides a benefit of simplifying the complex spectrum of GI microbiota.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1, a block diagram is provided showing aspects of an example computing system architecture suitable for implementing an embodiment of this disclosure and designated generally as example operating environment 100. Example operating environment 100 provides an aspect of a computerized system for compiling and/or running aspects of this disclosure including decision support tool and/or smart sensor apparatus, which may be incorporated into a decision support application. For example, in an embodiment, environment 100 may be used for monitoring, detecting or determining, and/or predicting a likely occurrence (or event) or future occurrence (or event) of microbiota-related changes or trends and the changes in relative concentration of an IgG subclass, as described herein, or other conditions in a patient, and additional decision support technology to facilitate caring for patients who may be prone to experience these conditions.

Operating environment 100 is one example of a suitable environment and system architecture for implementing an embodiment of the disclosure. Other arrangements and elements can be used in addition to or instead of those shown, and some elements may be omitted altogether for the sake of clarity. Further, as with operating environment 100, many of the elements described herein are functional entities that may be implemented as discrete or distributed components or in conjunction with other components, and in any suitable combination and location. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for system components or steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer (i.e., a computing device) as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Moreover, the components of operating environment 100, functions performed by these components, or services carried out by these components may be implemented at appropriate abstraction layer(s) such as the operating system layer, application layer, hardware layer, etc., of the computing system(s). Alternatively, or in addition, the functionality of these components and/or the embodiments described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. Additionally, although functionality is described herein with regards to specific components shown in example operating environment 100, it is contemplated that in some embodiments functionality of these components can be shared or distributed across other components.

Environment 100 includes one or more electronic health record (EHR) systems, such as EHR system(s) 160 communicatively coupled to network 175, which is communicatively coupled to computer system 120. In some embodiments, components of environment 100 that are shown as distinct components may be embodied as part of or within other components of environment 100. For example, EHR system(s) 160 may comprise one or a plurality of EHR systems such as hospital EHR systems, health information exchange EHR systems, clinical genetics/genomics systems, ambulatory clinic EHR systems, psychiatry/neurology EHR systems, and insurance, collections or claims records systems; and may be implemented in or as a part of computer system 120. Similarly, EHR system(s) 160 may perform functions for two or more of types of EHR systems (not shown). EHR system(s) 160 also may include records of physiological variables (such as vital signs measurements) obtained via one or more measurement apparatus, tests, or screenings, such as measurement device 141.

In some embodiments of the technologies described herein, aspects of a decision support tool for patients having or at risk for developing a condition or event occurrence, such a change or trend in microbiota-related activity and changes in relative concentration of an IgG subclass, as described herein, or recurrence of a condition or event may utilize data about a population of patients derived from patient EHR or other records information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system(s) 160 include one or more data stores of health-related records, which may be stored on storage 121, and may further include one or more computers or servers that facilitate the storing and retrieval of the health records. In some embodiments, EHR system(s) 160 and/or other records systems may be implemented as a cloud-based platform or may be distributed across multiple physical locations. EHR system(s) 160 may further include record systems, which store real-time or near real-time patient (or user) information, such as patient sensor(s) or monitor(s), support-surface, bedside, laboratory, or in-home patient monitors or sensors, for example, such as measurement device 141.

Example operating environment 100 further includes a user/clinician interface 142 and decision support application 140, each communicatively coupled through network 175 to an EHR system 160. Although environment 100 depicts an indirect communicative coupling between interface 142 and application 140 with EHR system 160 through network 175, it is contemplated that an embodiment of interface 142 or application 140 are communicatively coupled to EHR system(s) 160 directly. For example, in one embodiment a decision support application 140 operating at least in part on a client device (such as a user-operated computer device like a tablet) includes an interface 142 (which may comprise a graphical user interface), which may be used for accessing patient information from an EHR system(s) 160.

An embodiment of decision support application 140 comprises a software application or set of applications (which may include programs, routines, functions, or computer-performed services) residing on a client computing device (or distributed in the cloud and on a client computing device) such as a personal computer, laptop, smartphone, tablet, or mobile computing device. In an embodiment, the application is a Web-based application or applet, and may be used to provide or manage user services provided by an embodiment of the technologies described herein, which may be used by a caregiver or screener to provide, for example, information about the likelihood of a specific patient or population of patients to have or develop a condition or health event, such a change or trend in microbiota-related activity, as described herein, and may further include a degree or level characterizing the severity of the condition or event. In some embodiments, application 140 includes or is incorporated into a smart sensor or computerized decision support tool, as further described herein. Further, some embodiments of application 140 utilize user/clinician interface 142.

In some embodiments, application 140 and/or interface 142 facilitates accessing and receiving information from a user or health care provider about a specific patient or set of patients, according to the embodiments presented herein. Embodiments of application 140 also may facilitate accessing and receiving information from a user or health care provider about a specific patient, caregiver, or population including historical data; health care resource data; physiological variables or other patient-related measurements, time series, and predictions (including plotting or displaying the determined outcome and/or issuing an alert) described herein; or other health-related information, and facilitates the display of results, recommendations, or orders, for example. In an embodiment, application 140 also facilitates determining, receiving, or providing: notifications, recommendations, care plan changes, or orders, staffing scheduling, and/or queries from a user, which may be based on the results of monitoring and/or forecasted outputs, and which may in some embodiments utilize user interface 142. Decision-Support application 140 may also be used for providing diagnostic services or evaluation of the performance of various embodiments.

In some embodiments, user/clinician interface 142 may be used with application 140, such as described above. One embodiment of user/clinician interface 142 comprises a user interface that may be used to facilitate access by a user (including a clinician/caregiver such as a medical caregiver, physical therapist, or the like) to a probability, likelihood, forecast, score or prediction determined according to the technologies described herein, including information indicating a likelihood that a patient is undergoing a meaningful change or trend in microbiota-related activity, as described herein. One embodiment of interface 142 takes the form of a graphical user interface and application, which may be embodied as a software application (e.g., decision support application 140) operating on one or more mobile computing devices, tablets, smartphones, front-end terminals in communication with back-end computing systems, laptops, or other computing devices. Example embodiments of such graphical user interface are depicted in FIGS. 5A and 5B.

With reference to FIGS. 5A and 5B, example graphical user interfaces 500 and 550 are shown. These example embodiments of graphical user interfaces 500 and 550 are used with the decision support tool running a method 200 (described in FIG. 2). In particular, graphical user interface 500 depicts the results of determinations from method 200, shown at item 510, and (in this example embodiment) a determination (item 520) regarding the patient's likelihood of IBS-D or IBS-M being responsive to particular treatments. Some embodiments may also include a percentage or probability of the likelihood (item 530). In this way, the embodiments of a decision support tool (or smart sensor) may provide an indication of likelihood of the presence or absence of IBS and the joint significance of the microbiota and immunoglobulin G changes (if any) to the user clinician. In some embodiments, example graphical user interfaces 500 and 550 may be presented on a display, touch screen, monitor, of a computing system, such as computer system 120 described below. For instance, in one embodiment, graphical user interfaces 500 may be presented via an app (decision support application 140) on a smart phone (computer system 120).

Returning to FIG. 1A and user/clinician interface 142, in an embodiment, the application comprises or operates in conjunction with the PowerChart® software manufactured by Cerner Corporation. In an embodiment, interface 142 includes a Web-based application (which may take the form of an applet or app) or set of applications usable to manage user services provided by an embodiment of the technologies described herein.

In some embodiments, interface 142 may facilitate providing the output of the determined detections, analysis, measurements, forecast(s), probabilities (or score), recommendations, scheduling orders, providing instructions (such as measuring, recording, and/or otherwise obtaining vital signs or other physiological variable measurements), confirmations or notifications (which may include, for example, confirmation that information has been received or notifications that information has not been received and there may be an error in the measuring instrument, user operation of a measurement device, or measurement procedure), reminders (such as notifications to obtain a physiological measurement sample), or outputs of other actions described herein, as well as logging and/or receiving other feedback from the user/caregiver, in some embodiments. In an embodiment, interface 142 also facilitates receiving orders for the patient from the clinician/user, based on the results of monitoring and predictions. Interface 142 also may be used for facilitating diagnostic services or evaluation of the performance of various embodiments.

Example operating environment 100 includes measurement device 141 communicatively coupled through network 175 to an EHR system 160. In an embodiment, measurement device 141 (sometimes referred to herein as an patient-interface component) comprises one or more sensor components operable to acquire clinical or physiological information about a patient, such as various types of physiological measurements, physiological variables, or similar clinical information associated with a particular physical or mental state of the patient, which may comprise input data into a classifier component of a decision support tool, and which may be acquired periodically, continuously, as needed, or as they become available, and may be represented as one or more time series of measured variables.

In one embodiment, measurement device 141 comprises sensors for obtaining (and in some instances pre-processing or interpreting) measurements of microbiota-related information and immunoglobulin-G related information. In one embodiment, measurement device 141 comprises sensors for obtaining (and in some instances pre-processing or interpreting) non-invasive recording of vital signs or other physiological or patient-related data, which may be obtained continuously, periodically, or at irregular intervals. Accordingly, the term measurement is used broadly herein, and it is contemplated that in some embodiments, measurement device 141 may not perform measurement but may receive information about physiological parameters (such as genotypic or phenotypic information, other measurements such as heart rate (HR), blood pressure (e.g., systolic blood pressure or SBP), respiratory rate (RR), for example and without limitation) which may be measured, observed, or otherwise recorded. Some embodiments of measurement device 141 may comprise one or more sensors, an interface component, and/or processing/communications component (not shown).

For example, in some embodiments, measurement device 141 is a system configured to perform Bacterial rRNA sequencing from acquired specimens, such as fecal matter. The extraction may be performed or facilitated using a DNA extraction kit, such as the Epicentre ExtractMaster™ fecal DNA extraction kit. In one embodiment, measurement device 141 utilizes the Illumina MiSeq™ platform or the Illumina NextSeq 500™ platform for performing the microbiota sequencing. In one embodiment, the sequencing output may be further processed (or pre-processed) using the Illumina BaseSpace™ software. Alternatively, for embodiments utilizing MiSeq™ or NextSeq™, output files may be processed (or pre-processed) with bcl2fastq software.

Figure 3:
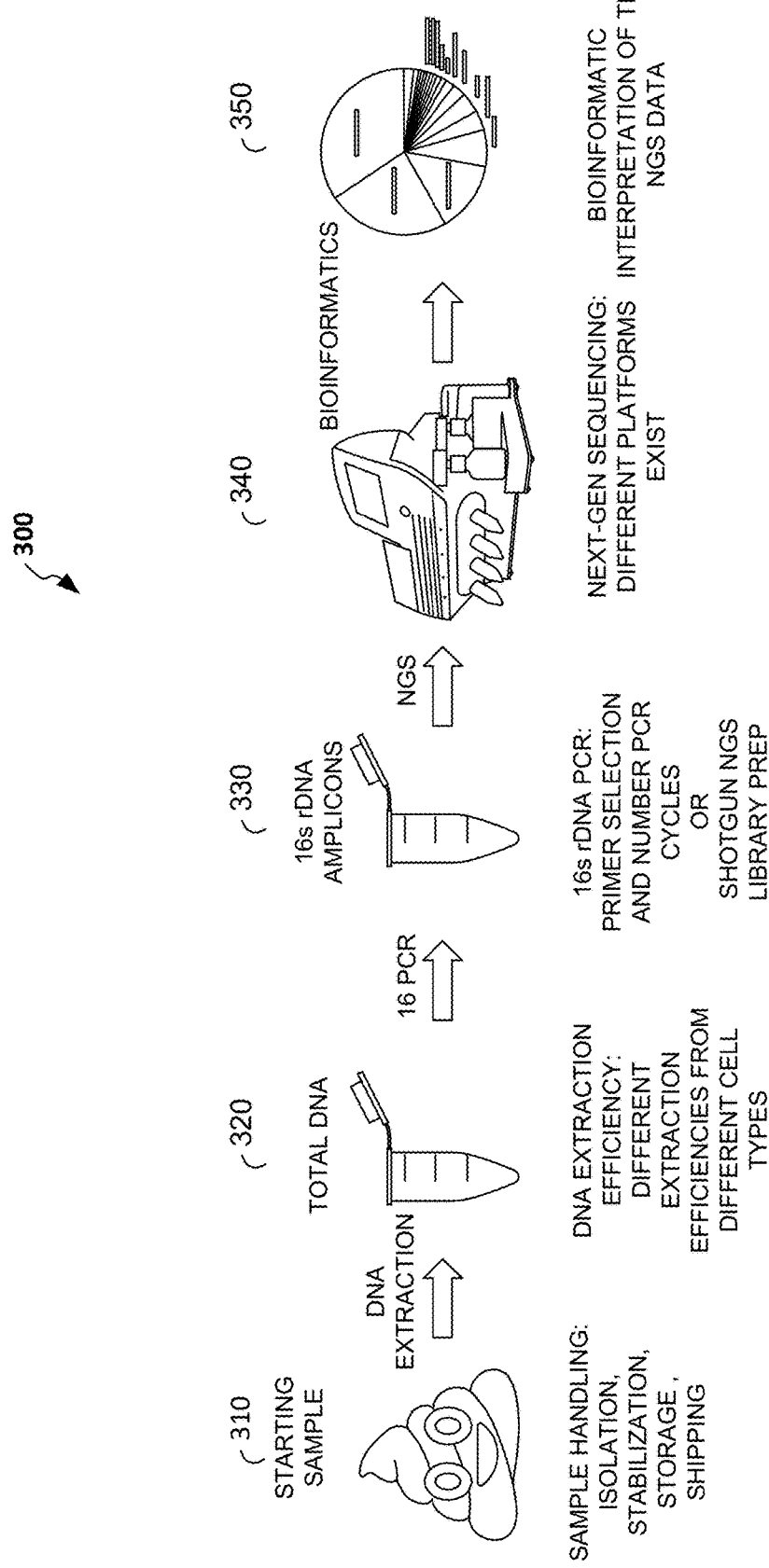
FIG. 3 depicts aspects of a process for 16S rRNA "next generation" sequencing of microbiota from a starting sample, which may be utilized by some embodiments of the disclosure.

FIG. 3 depicts aspects of an example process carried out by an example embodiment of measurement device 141, which is configured as a system for determining bioinformatic information from a starting sample (specimen) according to a process 300. Process 300 starts by receiving a staring sample at step 310. From this specimen, at step 320, DNA extraction is performed. At step 330, 16s rDNA amplicon sequencing (or similar genetic sequencing) may be performed to prepare for Next-Gen sequencing (or similar sequencing or processing) to obtain bioinformatic information provided in step 350. The 16s rDNA amplicon sequencing may comprise a 300-cycle 2×150 bp sequencing. FIG. 4 depicts an example of the 16s rRNA pyrosequencing results, which may be determined as part of the bioinformatics information using process 300 of FIG. 3. In particular, the table depicted in FIG. 4 comprises a table of OTUs and phylogenetic tree data.

Continuing with FIG. 1A, in some embodiments, measurement device 141 may include or utilize a Bluetooth or wireless communication data-transfer capability and may be wirelessly communicatively coupled with an application on a computing device, such as a smartphone an app or aspect of decision support application 140. In some embodiments, measurement device 141 comprises patient bedside monitor, such used in hospital, or a bathroom or toilet monitor, which may be embodied as a smart toilet. In an embodiment, one or more sensor components of measurement device 141 may comprise a user-wearable sensor component or sensor component otherwise integrated into the patient's environment. Examples of sensor components of measurement device 141 include a sensor positioned on an appendage (on or near the user's head, attached to the user's clothing, worn around the user's head, neck, leg, arm, wrist, ankle, finger, etc.); skin-patch sensor; ingestible or sub-dermal sensor; sensor component(s) integrated into the user's living environment (including the bed, pillow, or bathroom); and sensors operable with or through a smartphone carried by the user, for example. It is also contemplated that the clinical or physiological information about patient, such as the monitored variables and/or clinical narratives regarding the patient, used according to the embodiment of the invention disclosed herein may be received from other machine or human-performed (or human-guided) measurements, human observations, or automatically determined by sensors, which may be in proximity to the patient. For example, in one embodiment, a clinician periodically determines microbiota information for the patient and enters the measurement and/or observations via user/clinician interface 142. In another example, a nurse or caregiver enters one or more progress notes for an in-patient via user/clinician interface 142. Similarly, values for other physiological variables or patient data may be entered via user/clinician interface 142.

In addition to the microbiota and immunoglobulin-G (or subclasses) measurements, other examples of physiological variables monitored by measurement device 141, according to some embodiments, may include vital signs variables, such as heart rate (bradycardia and tachycardia) and blood pressure (hypotension and hypertension), oxygen saturation (peripheral desaturation), other vital signs, or physiologic or patient-related information as described herein, such as treatment regimens, diet, and other microbiota-related data. In some embodiments, microbiota-related information and immunoglobulin-G-related information are received by measuring device 141, and may be received or determined from lab results for the patient. In some embodiments these physiological variables monitored by measurement device 141 may include any type of measureable, determinable, or observable physiological or clinical variable or characteristic associated with a patient, which in some embodiments may be used for detecting changes or trends, forecasting a future value (of the measured variable, a composite variable based on one or more measured variables, or other factor determined at least in part from one or more measured variables) of a patient in order to facilitate clinical decision making. In an embodiment, a measurement device 141 comprises a sensor probe and a communication link that periodically transmits identification information and probe data to a decision support application 140, so that a time series of monitored values is stored in a record associated with the patient on an EHR system 160, thereby enabling the decision support application 140 to form a raw binary alarm indication and/or a physiological variable decision statistic.

Embodiments of measurement device 141 may store user-derived data locally or communicate data over network 175 to be stored remotely. Some embodiments of measurement device 141 include a monitor interface, which may be embodied as I/O such as buttons and sounds emitted from the measurement device 141, its firmware or software application or app operating on a user's mobile device or computer system 120, and in an embodiment may facilitate uploading of measured (or recorded, or otherwise received)

information from measurement device 141 to computer system 120. Additionally, some embodiments of measurement device 141 include functionality for processing user-derived information locally or for communicating the information to computer system 120, where it is processed. In some embodiments, the processing may be carried out or facilitated by one or more software agents, as described below. In some embodiments the processing functionality, performed on measurement device 141 and/or computer system 120 includes pre-processing and/or signal conditioning, such as removing noise or erroneous information.

Example operating environment 100 further includes computer system 120, which may take the form of one or more servers, and which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, aspects of application 140 or interface 142 may operate on or utilize computer system 120. Similarly, a portion of computing system 120 may be embodied on user interface 142, application 140, and/or EHR system(s) 160. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as local services or may be distributed across one or more components of operating environment 100, in the cloud, on one or more personal computers or servers such as system 120, and/or a computing device running interface 142 or application 140. In some embodiments, interface 142 and/or application 140 operate in conjunction with software stack 125.

Figure 2:
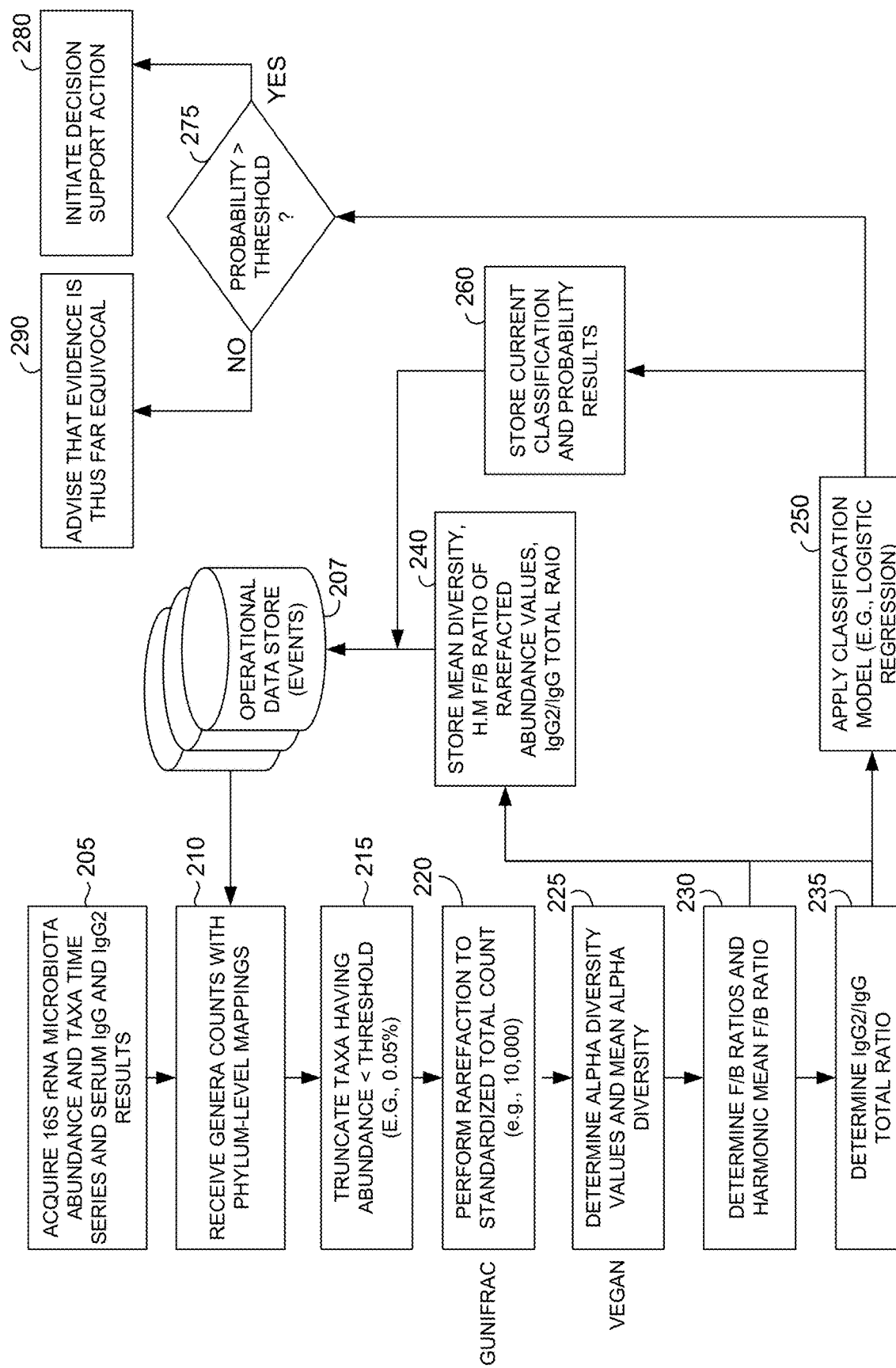
FIG. 2 depicts a flow diagram of a method for determining and monitoring microbiota diversity, ratio of phylum-level OTU counts, and relative IgG2 subclass concentration interpretations, and detecting a clinically significant alteration or trend, and initiating an action, in accordance with an embodiment of the disclosure.

In embodiments, model variables indexing (or mapping) service 122 and records/documents ETL service 124 provide services that facilitate retrieving patient variables such as physiological or other measurements, which may include frequent item sets, extracting database records, and/or cleaning the values of variables in records. For example, services 122 or 124 may perform functions for synonymic discovery, indexing or mapping variables in records, or mapping disparate health systems' ontologies, such as determining that a particular medication frequency of a first record system is the same as another record system. Some embodiments of stack 125 may also include predictive models service (not show), which in general is responsible for providing models such as multi-variable models, for detecting or predicting a particular condition or event utilizing a classifier apparatus to detect a conduction, such as a change or trend in microbiota-related activity. For example, in some embodiments, predictive model service determines and/or applies a classification model to determine the presence of statistically significant microbiota change and IgG2 subclass relative concentration change to the diagnosis or response treatment of the health condition of interest, such as further described in step 250 of method 200 (FIG. 2). In some embodiments, services 122, 124, and/or predictive models service may invoke computation services 126. In some embodiments, computation services 126 includes a predictive models service.

Computation services 126 may perform statistical software operations, calculations, and other determinations described herein, and may include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services. In an embodiment, computation services 126 and include computer-performed services or routines, which may be embodied as one or more software agents or computer program routines such as the example embodiments of computer program routines illustratively provided in FIGS. 7A-7C. In one embodiment, computation services 126 comprises the R-System GUniFrac package, for performing rarefaction or determining generalized UniFrac distances for comparison of microbial communities, and the vegan package for determining diversity measures. Additional details about example computation services 126 are provided in the example computer program routines of 7A-7C, and described further in connection to FIG. 2.

Computation services 126 also may include natural language processing services (not shown) such as Discern nCode' developed by Cerner Corporation, or similar services. In an embodiment, computation services 126 include the services or routines, which may be embodied as one or more software agents or computer software routines such as the example embodiments of computer program routines illustratively provided in FIGS. 7A-7C. Computation services 126 also may include services or routines for utilizing one or more classification models or processes, such as described in connection to FIG. 2 and the example computer program routines illustratively provided in FIGS. 7A-7C. In some embodiments, computation services 126 use EHR system(s) 160, model data and model storage services (not shown), and/or other components of example operating environment 100, and may also include services to facilitate receiving and/or pre-processing physiological (or other patient-related) data. For instance, model data and model storage services may be utilized to perform services for facilitating storage, retrieval, and implementation of the forecasting models described herein and of the data used in models, classifier apparatus, or predictive services.

In some embodiments, stack 125 includes file system or cloud-services 128. Some embodiments of component 128 may comprise an Apache Hadoop and Hbase framework, or similar frameworks operable for providing a distributed file system, and which in some embodiments facilitate provide access to cloud-based services, such as those provided by Cerner Healthe Intent®. Additionally or alternatively, some embodiments of file system or cloud-services 128 or embodiments of stack 125 may comprise one or more stream processing service(s). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient diagnoses or determinations, recommendations; recommendation knowledge base; recommendation rules; recommendations; recommendation update statistics; an operational data store, which stores events, frequent item sets (such as "X often happens with Y", for example), and item sets index information; association rule-bases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
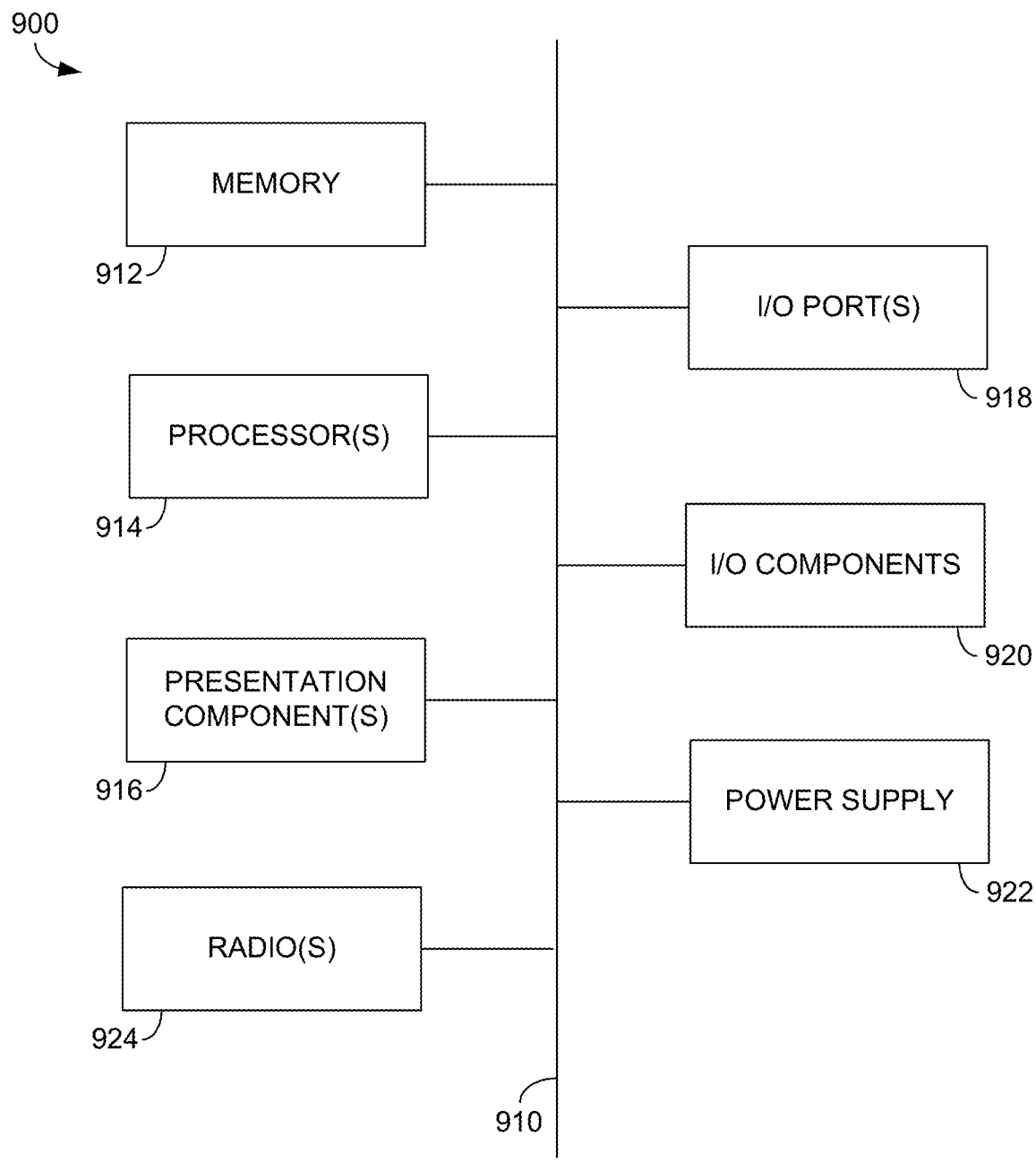

Turning briefly to FIG. 1B, there is shown one example embodiment of computing system 900 representative of a system architecture that is suitable for computer systems such as computer system 120. Computing device 900 includes a bus 910 that directly or indirectly couples the following devices: memory 912, one or more processors 914, one or more presentation components 916, input/output (I/O) ports 918, input/output components 920, radio 924, and an illustrative power supply 922. Bus 910 represents what may be one or more busses (such as an address bus, data bus, or combination thereof). Although the various blocks of FIG. 1B are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1B is merely illustrative of an example computing system architectures that can be used in connection with one or more embodiments of the present disclosure. Distinction is not made between such categories as "workstation," "server," "laptop," "hand-held device," etc., as all are contemplated within the scope of FIG. 1B and reference to "computing system."

Computing system 900 typically includes a variety of computer-readable media. Computer-readable media can be any available media that can be accessed by computing system 900 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 900. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above may be included within the scope of computer-readable media.

Memory 912 includes computer-storage media in the form of volatile and/or nonvolatile memory. The memory may be removable, non-removable, or a combination thereof. Exemplary hardware devices include solid-state memory, hard drives, optical-disc drives, etc. Computing system 900 includes one or more processors that read data from various entities such as memory 912 or I/O components 920. In an embodiment, storage 121 is embodied as memory 912. Presentation component(s) 916 present data indications to a user or other device. Exemplary presentation components include a display device, speaker, printing component, vibrating component, etc. In an embodiment, functionality provided via user/clinician interface 142 is facilitated by one or more presentation components 916.

In some embodiments, computing system 924 comprises radio(s) 924 that facilitates communication with a wireless-telecommunications network. Illustrative wireless telecommunications technologies include CDMA, GPRS, TDMA, GSM, LTE, WiMAX, and the like. Radio 924 may additionally or alternatively facilitate other types of wireless communications including Wi-Fi, Bluetooth, NFC, other types of RF communication, light, infrared, or the like. As can be appreciated, in various embodiments, radio 924 can be configured to support multiple technologies and/or multiple radios can be utilized to support multiple technologies.

I/O ports 918 allow computing system 900 to be logically coupled to other devices, including I/O components 920, some of which may be built in. Illustrative components include a microphone, joystick, game pad, satellite dish, scanner, printer, wireless device, etc. The I/O components 920 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 900. The computing system 900 may be equipped with depth cameras, such as stereoscopic camera systems, infrared camera systems, RGB camera systems, touchscreen technology, and combinations of these, for gesture detection and recognition. Additionally, the computing system 900 may be equipped with accelerometers or gyroscopes that enable detection of motion. While embodiments are employed using these computing systems, the focus of this application is the logical structures programmed into the computing system, since it is the logical structures that are carried out by the computer—not the computer components themselves—that realize the improvement over the drawbacks of the conventional industry practice.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Turning now to FIG. 2, one example embodiment is provided of a method 200 for conditionally initiating an intervening action for a patient with IBS based on detecting clinically significant alterations or trends of operational taxonomic units' (OTUs') relative abundances and diversity in combination with alteration in relative concentration of one or more immunoglobulin G (IgG) subclasses. In particular, method 200 generates and utilizes an embodiment of an improved smart sensor system for detecting and ascertaining meaningful changes or trends in fecal microbiota profiles at the 'phylum' taxonomic level, alpha diversity at the 'genera' taxonomic level, and serum immunoglobulin G subclass profiles. In the example embodiment of method 200, a joint machine-learning classifier model it utilized to determine the statistical significance. In some embodiments, the smart sensor system is a component of (or operate in conjunction with) a decision support tool. In one embodiment, the smart sensor comprises a computer-implemented sensor or software-based computerized sensor that utilizes the newly discovered aspects of physiological data of a patient, which may be received from laboratory measurements, and employs a novel process to derive new information from the aspects of physiological data, and then applies a classifier to ultimately detect clinically significant alteration or trend in microbiota diversity and immunoglobulin G subclass profiles, as described herein.

With reference to FIG. 2 and method 200, with respect to the embodiments of a decision support tool utilizing method 200, as well as some of the other embodiments described herein, at least one novel aspect comprises the detection and/or characterization of endotypes of functional gastrointestinal conditions, such as IBS, via a joint machine-learning classifier model that combines determinations of fecal microbiota profiles at the 'phylum' taxonomic level, alpha diversity at the 'genera' taxonomic level, and serum immunoglobulin G subclass profiles. High taxonomic level changes in microbiota are herein determined to be sufficient for diagnostic and treatment management purposes and may, indeed, be superior to measuring more detailed changes in lower-level taxa abundances, insofar as the wide variety of functional GI conditions and their polymorphic etiologies, the variety of treatments and differing mechanisms of action that evoke different responses by the body of the subject in whom measurements are made, the variety of clinical presentations and conditions' chronicity and comorbid diagnoses, and other factors comprise a combinatorial explosion of nosologic patterns such that exhaustively determining all the patterns would be cost-prohibitive or otherwise infeasible. For instance, if only a subset of the detailed patterns were evaluated there would be a high likelihood of negative results, and the negative results would be unhelpful to guide diagnosis or medical management.

Abundance weighted non-phylogenetic diversity measures such as Simpson and Shannon may be utilized in human microbiome methods. But in contrast, abundance-weighted phylogenetic diversity (PD) measures, as utilized by embodiments described in connection to FIG. 2, would not be typically utilized for this purpose. Abundance-weighted PD measures take a sum of branch lengths weighted by abundance, such that branches that connect abundant taxa get a higher weight than ones that do not. Thus, rare taxa and contaminant sequences are down-weighted compared with abundant taxa. The level of similarity between samples or groups of samples is called beta diversity. As with alpha diversity, classical measures applied to OTU counts may be used; however, phylogenetics-based methods may be utilized, and may be variants of the "UniFrac" PD metric.

In some embodiments, a generalized UniFrac distance is utilized. The weighted version of the UniFrac metric accounts for the relative abundance of each of the taxa within the communities, but this places too much emphasis on the most abundant taxa. The unweighted version of the UniFrac metric places too much emphasis on rare taxa or specimen contaminants. By contrast, the generalized UniFrac distance corrects the limitation of the weighted and unweighted UniFrac metrics by down-weighting their emphasis on abundant and rare taxa, respectively.

Such diversity metrics are sensitive to variable sequencing depth. Therefore, to compare microbiomes on an equal basis, some embodiments of the technologies described herein utilize a rarefaction method prior to determining diversity. Rarefaction curves are utilized for estimating species richness. Raw species richness counts, which are used to create accumulation curves, can be compared when the species richness has reached a clear asymptote. OTU species richness increases with sample size; differences in empirical richness may be caused by differences in sample size. Rarefaction curves produce smoother lines that facilitate point-to-point or full dataset comparisons. One can plot the number of species as a function of either the number of individuals sampled or the number of samples taken. The sample-based approach accounts for patchiness in the data that results from natural levels of sample heterogeneity. However, when sample-based rarefaction curves are used to compare taxon richness at comparable levels of sampling effort, the number of taxa should be plotted as a function of the accumulated number of individuals, not accumulated number of samples, because datasets may differ systematically in the mean number of individuals per sample. One cannot simply divide the number of species found by the number of individuals sampled in order to correct for different sample sizes. Doing so would assume that the number of species increases linearly with the number of individuals present, which is not in general the case.

Rarefaction may assume that the individuals in an environment are randomly distributed, the sample size is sufficiently large, that the samples are taxonomically similar, and that all of the samples have been collected and processed in the same manner. If these assumptions are not met, the resulting curves may be skewed. Rarefaction works well when no taxon is extremely rare or common or when beta diversity is very high. Rarefaction may assume that the detected number of a species reflects the sampling intensity, but if one taxon is especially common or rare, the measured count will be related to the extremity of the number of individuals of that species, not to the intensity of sampling. The technique may not account for specific taxa. It examines the number of taxons present in a given sample, but does not look at which OTUs are represented across samples. Thus, two samples that each contain N species may have substantially different compositions, leading to a biased estimate (under-estimation) of species richness. The technique may not recognize species abundance, but species richness. A better measure of diversity may account for both the number of species present and the relative abundance of each.

Accordingly, method 200 begins at step 205, wherein microbiota abundance and taxa information associated with a subject are received. For instance, serial or successive specimens may be acquired from an anatomical site (such as genitals or skin or pharynx) or specimen type (such as feces or blood or sputum) of a subject, such as a human patient or animal In one embodiment, the inter-sampling interval for the data measurements is not shorter than the cell-cycle generation time of microbiota in log-phase growth (for instance, 8 to 12 hours) and in some instances, may be at least several times a typical generation time. In the case of excreta, better results may be obtained where the inter-sampling interval is not shorter than the usual residence time of a bolus passing through the length of the viscus (thus for gut, approximately 24 hours).

From the specimens, abundances of microbial and/or taxa are measured, and from the serial or successive samples, a time series is formed. Approximately contemporaneously (or within a similar time interval of each of the microbiota specimen collections) serum specimens of immunoglobulin G are also acquired form the subject. For each serum specimen, IgG2 subclass concentration is determined and expressed as a fraction of total serum IgG, thereby forming an IgG time series. Some embodiments may begin by determining or receiving measurement data from the microbiota-related and serum specimens. The determined taxa abundance data and IgG2 subclass concentration data may be stored until enough samples are acquired to comprise time series of sufficient length, which may be predetermined or based on a particular condition of the subject, a treatment, as described herein. In an embodiment, the serum specimen measurements may be determined from the subject and collected at a time approximately contemporaneous with the collection of the at least 4 fecal specimens.

In an embodiment, 16S rRNA sequencing methods are utilized, which may include amplification, depending on the total count of organisms in the specimens and the efficiency of nucleotide extraction. Some embodiments begin by determining or receiving measurement data from the specimens to determine the time series. In some embodiment, the measurements may be received from an electronic health record associated with the patient (such as EHR 160), may be received from lab results or smart sensor or measurement device, such as measurement device 141 (FIG. 1A) for example.

In embodiments of step 205, the specimens may be associated with a diagnostic health condition of interest in the subject sampled, such as IBS, with one or more taxa pertinent to management of the health condition, and with the subject's treatment metadata (or condition metadata) corresponding to the collection date on which each specimen was acquired. Further, some embodiments of step 205 include associating a particular patient with the measurement device 141, system, or data stream, and/or binding information about the patient or patient's EHR and initializing a data.frame (e.g., attributes and current date) for acquiring the microbiota information.

The determined taxa abundance and metadata may be stored until enough samples are acquired to comprise a time series of sufficient length. In one embodiment, a time series of at least three specimens is determined. In other embodiments, the time series may comprise eight specimens, and in some embodiments, two specimens may be used (or a shorter time series), but results may be degraded (e.g., resulting in a lower specificity or sensitivity).

Next, at step 210, based on the measurement information from step 205, determine genera counts with phylum-level mappings. In some embodiments, measurement device 141 may be used to determine these counts, or the counts may be determined based on information received from measurement device 141 or the information determined in step 205. After accumulating enough measurement data to determine a time series of sufficient length, then the taxa may be filtered or truncated, at step 215, to retain genera-level taxa having abundance greater than a threshold value, such as 0.05%, according to one example embodiment actually reduced to practice and described herein, and the phylum-level membership information for each retained genus OTU. In one embodiment, the threshold value is pre-determined and comprises 0.05%. In another embodiment, the threshold is determined based on the patient's condition, the patient's treatment, or may be set by a clinician or caregiver.

Some embodiments of method 200 may further determine a phylogenetic tree matrix so as to enable determination of phylogenetic-distance-based diversity metrics. In particular, the genetic distance may be determined using the Kimura 2-parameter (K80) model. For instance, in an embodiment, a phylogenetic tree matrix with may be performed by Unweighted Pair Group Method with Arithmetic Mean (UPGMA) methods on the K80 distance matrix, for the taxa represented in the time series.

At step 220, rarefaction may be performed on each sample's taxa abundances thereby normalizing counts to a standard count. In some embodiments, such as in the case of in the case of fecal microbiota time series, N may be approximately 10,000. Some embodiments of step 220 utilize computation services 126, which may include the R-system GUniFrac package.

At step 225, the alpha diversity of the bacterial taxa of each member of the time series is determined, and the mean alpha diversity is determined. In one embodiment, the microbiota diversity determined in step 225 is a numerical alpha diversity or a generalized phylogenetic-distance UniFrac diversity, which may be calculated for each time series member. The UniFrac diversity may be variance-adjusted. In one embodiment, the alpha diversity (for example, Shannon, Simpson, or Chao) may be determined for each time series member. The mean alpha diversity may be determined as the arithmetic mean of the diversity values of the microbiota-related time series measurements. Additionally, in some embodiments of step 225 further comprise, the rarefied relative abundances of genera in the phylum Firmicutes are totalized and the rarefied relative abundances of genera in the phylum Bacteroidetes are totalized in each of the time series of measurement specimens. Some embodiments of step 225 may also utilize computation services 126, which may include the R-system vegan package. (See e.g., the example computer program routines of FIGS. 7A and 7B.)

At step 230, the Firmicutes to Bacteroidetes ratio (F/B ratio) may be determined for each member of the time series of measurement specimens, and further determine the harmonic mean of the determined F/B ratios. In some embodiments of step 230, a composite variable may be created from the harmonic mean of the F/B ratios and the mean diversity determined from step 225. In one embodiment, the composite variable is the ratio of the F/B ratio harmonic mean to the mean diversity from step 225. In one embodiment, the harmonic mean of the plurality of F/B ratio values may be substituted by the geometric mean of the plurality of the F/B ratio values.

Following a flare of IBS symptoms, fecal microbiota dysbiosis may be detected in the gut microbiota in severely symptomatic IBS patients. The biodiversity of gut bacteria is initially decreased, and then may return to near-normal levels. In addition, genera of phylum Firmicutes are increased in abundance, abundances of genera of phylum Bacteroidetes are decreased, and the ratio of Firmicutes counts to Bacteroidetes counts (F/B ratio) is thereby increased. After effective treatment, the majority is a beneficial genus, *Bacteroides*. and the F/B ratio may be restored to a lower, near-normal level.

At step 235, Determine the concentrations of total IgG and of IgG subclass 2 (IgG2). In particular, embodiments of step 235 determine the relative concentration of immunoglobulin G (IgG) subclasses in the serum specimen measurements. For instance, the IgG2 subclass concentration may be determined as a fraction of total serum IgG, as described above. Thus a ratio of serum IgG2 concentration to total IgG concentration per specimen measurement may be determined for each measurement of the IgG time series. Alternatively, in some embodiments, step 235 comprises calculating the logarithm of IgG2 concentration and the logarithm of total IgG concentration, and then calculating the ratio of these log-transformed values. In some embodiments, the IgG2 subclass concentration and total IgG concentration values that are transformed, such as via the logarithmic transformation, to ameliorate skewness in the raw concentration values' statistical distributions. For instance, the IgG subclasses' concentrations and the total IgG concentration may be right-skewed and approximately log-normally distributed. In some embodiments, logarithmic transformation of the raw concentrations may be performed prior to performing inferential statistical analyses.

At step 240, the determined mean diversity, harmonic mean F/B ration or rarefacted abundance values, and IgG2/ IgG total ratio determinations are stored in operation data store 207 (which may be embodied as storage 121 of FIG. 1A) so as to be accessible for future analyses upon acquiring additional specimens.

At step 250, a classification model may be determined and applied. In some embodiments of step 250, a machine-learning model is constructed whereby the variables' values may be combined to produce a numerical probability of the presence of the functional gastrointestinal condition subject. In some embodiments, the classification model is determined to utilize the determined arithmetic mean of the diversity values (step 225), the harmonic mean of the F/B ratio (or the output of step 230), and the ratio of IgG2 to IgG (step 235), to determine the presence of statistically significant microbiota change and IgG2 subclass relative concentration change to the diagnosis or response treatment of the health condition of interest. For example, in an embodiment, a logistic regression model is utilized. In other embodiments, the classification model may comprise or be based on a neural network, random forest, support vector machine, decision tree, bagging or boosting, or other machine-learning modeling means for classification. In this way, the joint evidence from these determinations is combined to further ascertain the likely effectiveness of a medical treatment that is directed to microbiota profile, microbiota diversity, or immune response in the subject.

Several advantages are provided by those embodiments where logistic regression is used as the means of constructing the classifier model. For instance, in these embodiments using logistic regression, then in step 235, no transformation of IgG subclass concentration or IgG total concentration may be needed. This is because logistic regression does not require a linear relationship between the dependent and independent variables. Second, the error terms (residuals) may not need to be normally distributed. Third, homoscedasticity may not be required.

However, where certain machine-learning methods of classifier construction which are sensitive to skewedness or outliers are utilized (such as neural networks, K-nearest neighbor, or naive Bayes, for example), the skewedness of the raw variables may be problematic. In particular, if two random variables are lognormal then the ratio of the two log-normally distributed random variables also follows a lognormal distribution. Therefore, in one embodiment the ratio of IgG2 concentration to total IgG is transformed (e.g., in step 235) before proceeding with subsequent modeling steps. In another embodiment, the IgG2 and total IgG concentrations are first log-transformed and then the ratio of the log-transformed concentrations is calculated prior to proceeding with modeling step 250 of method 200. If $IgG2/IgG_{total}$ «(as is commonly the case in healthy normal individuals), then $-\ln(1-IgG2/IgG_{total}) \sim IgG2/IgG_{total}$. Therefore, in some embodiments, a derived variable equal to $-\ln(1-IgG2/IgG_{total})$ is calculated (in step 235 or in step 250) for use in subsequent modeling of step 250.

At step 260, the resulting condition classification, probability, and likely treatment effectiveness may be stored in persistent machine-readable storage, such as data store 207 or storage 121 (FIG. 1A), and may be subsequently utilized to determine whether to initiate an intervening action, such a providing a notification to an attending clinician that includes an advisory interpretation based on the model's classification and/or based on the input determinations (i.e., the outputs of steps 225, 230, and 235).

The probability results from the classification model may be compared against a threshold for statistical significance. In an embodiment, this comparison comprises determining the p value and comparing it against a threshold. For example, where the p value is determined to be less than 0.05 (or by way of example in another embodiment less than or equal to 0.05), then statistical significance is determined. In some embodiments, the threshold may be pre-determined based on the subject's or patient's condition, or based on rules or preferences of a healthcare entity or clinician, or the previous outcomes of method 200.

Accordingly, at step 275, where the classification model determines statistical significance (e.g., joint statistical significance is determined), then method 200 proceeds to step 280, where the decision support tool running method 200 may initiate a decision support action, such as an intervening action, as described herein. For instance, a notification may be provided to a caregiver that a significant change has occurred in the subject, and/or another intervening action may be initiated or otherwise carried out. For instance, one intervening action comprises generating a notification that may be emitted or otherwise communicated to the patient or to a caregiver, such as a provider clinician responsible for the care of the patient. For example, an electronic advisory or warning message may be emitted to a human user, such as a caregiver, indicating a significant change in microbiota-related levels, which may indicate a change (or possible future change) in the patient's condition or that the current treatment is impacting the microbiota in a manner that may merit intervening treatment. In an embodiment, the action comprises generating and emitting or communicating the notification, which may be emitted/communicated via a bedside or patient-side alarm, user/clinician interface (such as interface 142 described in FIG. 1A), or may be communicated to a smartphone or personal computing device of a caregiver, thereby alerting them of a possible change to the patient's condition.

Another intervening action that may be initiated, based on the determined likelihood, comprises modifying a care plan or treatment procedure or a recommendation for modifying a care plan or treatment procedure associated with the patient; for example, automatically scheduling an appointment with a specialist or other healthcare resources for the patient, operating on the patient, or administering another similarly effective therapeutic intervention, such as changing the patient's treatment or diet. The recommendation may be provided in conjunction with a notification, and/or may be provided via a user/clinician interface, such as interface 142, described in connection with FIG. 1A.

Yet another action that may be initiated, based on the determined likelihood, comprises automatically modifying computer code executed in a healthcare software program for treating the patient, thereby transforming the program at runtime. For example in one embodiment, the modification comprises modifying (or generating new) computer instructions to be executed at runtime in the program, the modification may correspond to a change in a care plan, treatment procedure, or therapeutic intervention to be administered to the patient due to the determined joint significance. In one instance, the modification comprises changing the executed computer instructions corresponding to monitoring the patient's condition, such as increasing the frequency of obtaining physiological measurements of the patient, or increasing sensitivity of monitoring physiological changes in a patient.

Yet another action that may be initiated, based on the determined likelihood, comprises scheduling healthcare resources for the patient. For example in one embodiment, a physical therapy resource may be automatically reserved for the patient, healthcare staff may be notified and/or automatically scheduled, or transportation/support staff or resources for getting the patient to a healthcare facility may be called. In one embodiment, this action comprises modifying or updating a resource/scheduling electronic record in a resource/scheduling system, such as operated as part of a hospital or healthcare system. In one embodiment, the action comprises, upon a determined significance of microbiota-related change or trend, initiating a computer instruction that modifies the scheduling healthcare resources, which may include computer instructions for automatically alerting, scheduling, and/or notifying staff, reserving rooms, transportation, or other equipment/space, and which may include changing the priority of the patient (when compared to other patients) for receiving these resources.

Otherwise, according to the embodiment shown in FIG. 2, where joint significance is not determined (e.g., the p value does not satisfy the threshold), then method 200 proceeds to step 290. In some embodiments, or step 290 method 200 may log a data entry (or emit a notification) indicating that the comparative non-superiority and non-inferiority of the two or more time periods and their respective treatment regimens can be emitted. Alternatively, some embodiments of step 290 do not emit a notification, and instead may wait until method 200 repeats for a future time period using next or subsequently specimen information. As described previously, an aspect of a decision support tool, comprising a computer program routine and implementing an embodiment of method 200 is illustratively provided in FIGS. 7A-7C.

Example Reduction to Practice

An illustrative example embodiment of the present disclosure that has been actually reduced to practice is described herein. This example embodiment comprises a decision support tool which utilizes an improved smart sensor to detect statistically meaningful changes or trends in microbiota-related activity of the patient and relative concentration of an IgG subclass, as described herein, and upon such detection, initiates a responsive intervening action. However, it should be noted that although this example reduction-to-practice focuses specifically on a specimen type or anatomical site (e.g., intestinal [fecal] microbiota) and on one health condition (irritable bowel syndrome), embodiments of the technologies described herein are more generally applicable to serial microbiota measurements from any of a variety of anatomical sites or specimen types and any of a variety of health conditions.

With reference to FIGS. 1A, 3, 7A-7C, and with continuing reference to method 200 of FIG. 2, this example embodiment was constructed, tested, and verified as described below. Informed consent was performed in 21 healthy control subjects and in 19 subjects with symptomatic IBS-D or IBS-M ('D': diarrhea-predominant; 'M': mixed or alternating diarrhea-and-constipation). Three stool samples were collected at 24—to 48-hour intervals from participating subjects with a sterile cotton swab, dispersed into a vial containing preservative, stored at refrigerator temperature until shipping, and shipped by surface mail to the laboratory for processing.

Upon receipt of specimens at the performing laboratory, Epicentre ExtractMaster™ fecal DNA extraction kits were used to extract nucleotides from the specimens. Approximately 700 ng of DNA were extracted from each sample. Group, genus, and species-specific 16S rRNA determinations were performed. Bacterial rRNA sequencing was performed on the Illumina MiSeg™ platform or the Illumina NextSeq 500™ platform. A 300-cycle 2×150 bp read configuration was utilized, yielding outputfiles of approximately 1.2 GB each. Output files were processed with Illumina BaseSpace™ software. Alternatively, MiSeg™ or NextSeg™ output files were processed with bcl2fastq software. To reduce the quantitative error of the detected bacteria OTUs and to characterize the changes in bacterial copies, the abundance of 16S rRNA gene copies was calculated from standard curves, and specific bacterial taxons were expressed as a percentage of the total bacteria determined by the universal primers.

As described in the description of method 200, samples with more than 10,000 reads were rarified to 10,000 reads (step 220 of method 200), and taxa having abundance less than 0.05% were censored (step 215 of method 200). Rarefaction was performed using the GUniFrac package in R and Shannon diversity measures were determined using the vegan package in R. The arithmetic mean of Shannon diversity values of the three specimens was calculated (step 225 of method 200), and the harmonic mean of Firmicutes-to-Bacteroidetes count ratios was determined (step 230 of method 200). From the harmonic mean F/B ratio and the mean diversity was created a composite variable comprised as the ratio of the harmonic mean F/B ratio to the mean diversity. The ratio of serum IgG2 to total IgG concentration was calculated (step 235 of method 200). Logistic regression was performed, regressing the composite variable and the IgG2/IgG$_{total}$ ratio on IBS status in the cohort of 40 persons, to create a statistical classifier model (Step 250 of method 200). The model was validated in a separate cohort of 67 subjects (30 with IBS-D or IBS-M; 37 healthy controls).

In this example embodiment, a computer system 120 running the Linux operating system (129) was utilized with the open-source software package R, and the R packages (computation services 126): GUniFrac and vegan packages. This example embodiment also used the example computer program routines provided in FIGS. 7A-7C.

Figures 6A, 6B:
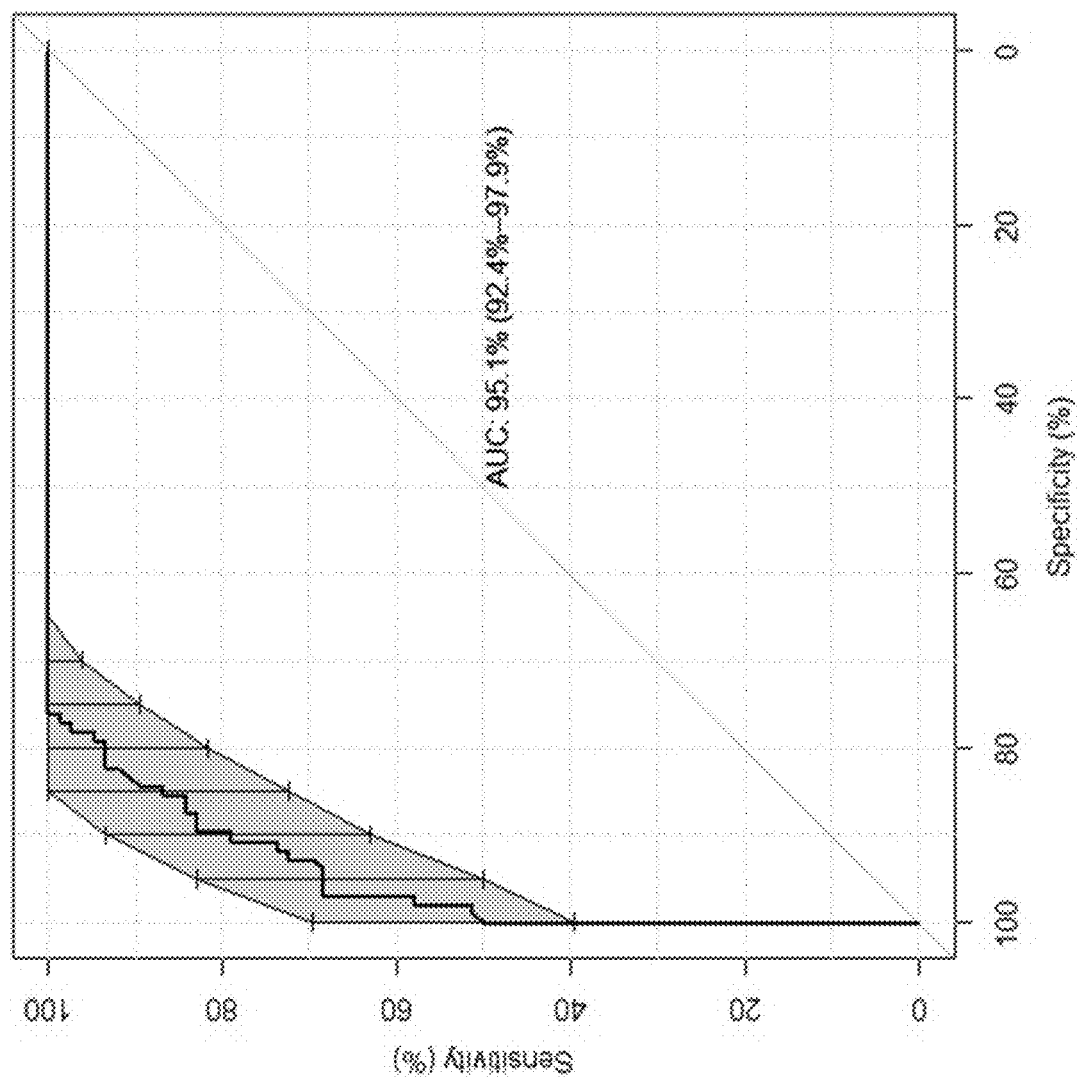
FIGS. 6A and 6B depict statistical performance of an example embodiment of the present disclosure actually reduced to practice, including a receiver operating characteristic (ROC) curve and table of statistical performance metrics indicating an improvement over the conventional technologies.

FIGS. 6A and 6B depict statistical performance of this example embodiment actually reduced to practice, including a receiver operating characteristic (ROC) curve for IBS prediction (FIG. 6A) and table of statistical performance metrics (FIG. 6B) indicating an improvement over the conventional technologies for detecting (or diagnosing, or determining an prognosis of) IBS, as described above. FIG. 7C illustratively provides an example embodiment of a computer program routine for generating the ROC curve shown in FIG. 5A.

As used herein and in connection with the claims listed hereinafter, the terminology "any of clauses" or similar variations of the terminology is intended to be interpreted such that features of claims/clauses may be combined in any combination. For example, an exemplary clause 4 may indicate the method/apparatus of any of clauses 1 through 3, which is intended to be interpreted such that features of clause 1 and clause 4 may be combined, elements of clause 2 and clause 4 may be combined, elements of clause 3 and 4 may be combined, elements of clauses 1, 2, and 4 may be combined, elements of clauses 2, 3, and 4 may be combined, elements of clauses 1, 2, 3, and 4 may be combined, and/or other variations. Further, the terminology "any of clauses" or similar variations of the terminology is intended to include "any one of clauses" or other variations of such terminology, as indicated by some of the examples provided above.

Clause 1. A computerized system that is a decision support tool for facilitating prognosis and treatment of a patient having a functional gastrointestinal condition, the system comprising: a processor; computer memory having instructions stored thereon that when executed by the processor perform operations comprising: from a first series of specimens acquired from the patient, determining a microbiota-related time series comprising measurements of microbiota abundances or taxa; from a second series of specimens acquired from the patient, determine an immunoglobulin G (IgG) subclass concentration thereby forming an IgG time series; receiving patient metadata associated with the measurements of the microbiota-related time series; based on the microbiota-related time series, performing rarefaction on each measurement's taxa abundances and normalizing taxon counts to a standard count; determining a microbiota diversity value for each measurement in the microbiota-related time series, thereby forming a diversity time series; determining, based on the diversity time series, determining a mean diversity; determining, based on the IgG time series, a Firmicutes to Bacteroidetes ratio (F/B ratio) and a harmonic mean of the F/B ratio; determine a relative concentration of immunoglobulin G (IgG) subclass in the IgG time series thereby comprising a IgG subclass ratio; based on the determined mean of the diversity values, the determined harmonic mean of the F/B ratio, and the determined ratio of IgG2 to IgG, utilizing a classification model to determine a joint statistical significance of microbiota change and IgG subclass relative concentration change; based on a determined statistical significance, determining a likelihood of Irritable Bowel Syndrome (IBS) conditions in the patent, and causing an intervening action regarding the human patient to be initiated.

Clause 2. The system of clause 1, wherein the intervening action comprises at least one of: issuing a notification to a caregiver associated with the patient; automatically scheduling healthcare resources for treating the patient; or modifying a computer program associated with a care plan for the patient.

Clause 3. The system of clauses 1 or 2 further comprising, determining genera counts with phylum-level mappings from the first specimens.

Clause 4. The system of clause 3, wherein the determined genera counts with phylum-level mappings correspond to the microbiota-related time series.

Clause 5. The system of clause 3, wherein the determining the genera counts with phylum-level mappings comprises determining and totalizing rarefied relative abundances of genera in the phylum Firmicutes, and determining and totalizing rarefied relative abundances of genera in the phylum Bacteroidetes in each measurement of the microbiota-related time series.

Clause 6. The system of any of clauses 1-5 further comprising, based on a determined statistical significance, determining a likelihood of a patient's IBS condition being responsive to a particular treatment.

Clause 7. The system of clause 6, wherein the treatment comprises administering eluxadoline, alosetron, or rifaxmin.

Clause 8. The system of any of clauses 1-7 further comprising, based on a determined statistical significance, determining a likelihood of the presence or absence of IBS.

Clause 9. The system of any of clauses 1-8, wherein the patient metadata associated with the measurements of the microbiota-related time series comprises metadata associated with an IBS condition.

Clause 10. The system of any of clauses 1-9, wherein the determined diversity value comprises an alpha diversity, and wherein the determined mean diversity comprises the mean alpha diversity.

Clause 11. The system of any of clauses 1-10, wherein the mean alpha diversity is determined as the arithmetic mean of the diversity values of the microbiota-related time series measurements.

Clause 12. The system of any of clauses 1-11, further comprising assembling a phylogenetic tree matrix with distance metric for the taxa represented in the time series.

Clause 13. The system of clause 12, wherein a Kimura 2-parameter (K80) model is utilized and the phylogenetic tree matrix is determined by Unweighted Pair Group Method with Arithmetic Mean (UPGMA) methods on the K80 distance matrix, for the taxa represented in the time series.

Clause 14. The system of any of clauses 1-13, further comprising filtering the taxa to retain genera-level taxa having abundance greater than a threshold.

Clause 15. The system of clause 14, wherein the threshold is 0.05%.

Clause 16. The system of any of clauses 1-15, wherein the microbiota diversity determination comprises abundance-weighted phylogenetic diversity (PD).

Clause 17. The system of any of clauses 1-16, wherein the first series of specimens are acquired from an anatomical site (such as genitals or skin or pharynx) or specimen type (such as feces or blood or sputum) of the patient.

Clause 18. The system of any of clauses 1-17, wherein the second series of specimens comprise serum specimens of immunoglobulin G, wherein the IgG subclass comprises IgG2, and wherein the relative concentration of IgG subclass (IgG subclass ratio) is determined as a fraction of IgG2 to total serum IgG.

Clause 19. The system of any of clauses 1-18, further comprising determining a composite variable from the harmonic mean of the F/B ratios and the mean diversity, as the ratio of the F/B ratio harmonic mean to the mean diversity.

Clause 20. The system of any of clauses 1-19, wherein the classification model comprises a machine learning model.

Clause 21. The system of any of clauses 1-20, wherein the classification model comprises a logistic regression model.

Clause 22. The system of any of clauses 1-21, wherein the first series of specimens is determined from serial samples form the patient.

Clause 23. The system of any of clauses 1-22, wherein the series of measurements is determined utilizing 16S rRNA sequencing.

Clause 24. The system of any of clauses 1-23, wherein each measurement in the time series is received at an inter-sampling interval equal or greater than the cell-cycle generation time of the microbiota in log-phase growth.

Clause 25. The system of any of clauses 1-24, wherein the time series comprises measurements from at least three serial specimens.

Clause 26. A computerized diagnostic method for determining a prognosis of IBS in a subject suffering from a functional gastrointestinal condition, the method comprising: acquiring at least three serial specimens from the subject, the specimens including serum; from the specimens, determining a measurement of abundances of microbial taxa thereby forming a time series; from the serum specimens, determining an IgG2 subclass concentration as a fraction of the total serum IgG; receiving treatment metadata for a health condition of interest, the treatment metadata associated with the time series; performing rarefaction on each sample's taxa abundances, normalizing taxon counts to a standard count; calculating microbiota diversity each member of the specimen series; determining a Firmicutes/Bacteroidetes (F/B) ratio of the rarefied abundances; determining the harmonic mean of the F/B ratio values; determining the arithmetic mean of the diversity values; applying a machine learning model that combines the arithmetic mean of the diversity values, the harmonic mean of the F/B ratio, and the ratio values of IgG2 to IgG, to determine a joint statistical significance of microbiota change and IgG subclass relative concentration change; based on the determined joint statistical significance, determining a likelihood of the presence of the functional gastrointestinal condition; and presenting an indication of the determined likelihood of the presence of the functional gastrointestinal condition.

Clause 27. The method of clause 26, further comprising based on the determined joint statistical significance, determining the likely effectiveness of a medical treatment that is directed to microbiota profile, microbiota diversity, or immune response in the subject.

Clause 28. The method of clauses 26 or 27, wherein the functional gastrointestinal condition of interest is irritable bowel syndrome (IBS), of diarrhea-predominant, constipation-predominant, or mixed type.

Clause 29. The method of any of clauses 26-28, wherein determining a measurement of abundances of microbial taxa comprises applying a 16S rRNA sequencing method including amplification, depending on the total count of organisms in the specimens and the efficiency of nucleotide extraction, and the resulting taxa abundance and metadata are stored in machine-readable persistent storage.

Clause 30. The method of any of clauses 26-29, wherein the specimens are from an anatomical site (such as the colon or ileum) or of a particular type of specimen (such as feces or blood or sputum).

Clause 31. The method of any of clauses 26-30, wherein determination of operational taxonomic units (OTUs) in each specimen is performed by pyrosequencing of 16S microbial rRNA.

Clause 32. The method of clause 31, wherein the determinations of OTUs in serial specimens are repeated and periodic sampling of a site or specimen type in a subject, such that the period of sampling is a longer time interval than is required for evolution of the microbiome in the site, under the conditions that are pertinent to the intended diagnostic or therapeutic purpose.

Clause 33. The method of clause 32, wherein a minimum sampling time-period for serial specimen collection (inter-sampling interval) is not shorter than the cell-cycle generation time of microbiota in log-phase growth (8 to 12 hours) and is at least several times a typical generation time or greater in length than three-fold multiple of cell-cycle times for the predominating OTUs, or 36 hours, whichever is greater.

Clause 34. The method of clause 33, wherein for excreta, the inter-sampling interval is not shorter than the usual residence time of a bolus passing through the length of the viscus, which for gut specimens is approximately 24 hours.

Clause 35. The method of any of clauses 26-34, further comprising assembling a phylogenetic tree matrix with distance metric for the taxa represented in the time series.

Clause 36. The method of any of clauses 26-35, wherein singleton OTUs that are detected in only one of the serial specimens have been discarded.

Clause 37. The method of any of clauses 26-36, wherein the measured taxa are filtered, retaining only genera-level taxa for subsequent steps along with phylum membership information for each of the retained genera.

Clause 38. The method of any of clauses 26-37, wherein only taxa having abundance greater than a threshold value of 0.05% of the total microbial count are retained for subsequent steps.

Clause 39. The method of any of clauses 26-38, wherein the series of specimens is associated with a diagnostic health condition of interest in the subject sampled, with one or more taxa pertinent to management of the health condition, and with the subject's treatment metadata corresponding to the collection date on which each specimen was acquired.

Clause 40. The method of any of clauses 26-39, wherein a phylogenetic tree matrix with distance metric is determined so as to enable determination of phylogenetic-distance-based diversity metrics, where the tree matrix is calculated preferably by UPGMA methods on the K80 distance matrix.

Clause 41. The method of any of clauses 26-40, wherein the value of the standard microbial count for rarefaction is approximately 10,000 in the case of a fecal microbiota time series.

Clause 42. The method of any of clauses 26-41, wherein the microbiota diversity is a numerical alpha diversity (for example, Shannon, Simpson, or Chao) or a generalized phylogenetic-distance UniFrac diversity.

Clause 43. The method of any of clauses 26-42, wherein the harmonic mean of the plurality of F/B ratio values is substituted by the geometric mean of the plurality of the F/B ratio values.

Clause 44. The method of any of clauses 26-43, wherein the composite variable comprised of the harmonic mean of F/B ratios and the mean diversity is constructed as the ratio of harmonic mean F/B to mean diversity.

Clause 45. The method of any of clauses 26-44, wherein the relative serum IgG2 subclass concentration as a fraction of the total serum IgG concentration is optionally substituted by IgG2 subclass concentration and total IgG concentration values that are transformed to ameliorate skewness in the raw concentration values' statistical distributions.

Clause 46. The method of any of clauses 26-45, wherein the transformation is a logarithmic transformation.

Clause 47. The method of any of clauses 26-46, wherein the machine-learning classification model is a logistic regression-based model.

Clause 48. The method of any of clauses 26-47, wherein an advisory interpretive message regarding the joint significance of the changes, if any, is electronically emitted to a caregiver associated with the subject.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A computerized system that is a decision support tool for facilitating prognosis and treatment of a patient having a functional gastrointestinal condition, the system comprising:
   a processor;
   computer memory having instructions stored thereon that when executed by the processor perform operations comprising:
      generating a first set of time-series data comprising measurements from a first series of specimens acquired from the patient, wherein the measurements represent microbiota abundances or taxa;
      generating, from a second series of specimens acquired from the patient, a second set of time-series data, the second set of time-series data comprising values representing immunoglobulin G (IgG) subclass concentrations;
      obtaining patient metadata associated with the measurements of the first set of time-series data;
      generating a third set of time-series data at least by:
         performing rarefaction on each taxa abundances of each measurement of the first set of time-series data to normalize taxon counts to a standard count;
      generating a fourth set of time-series data at least by:
         determining a microbiota diversity value for each measurement in the third set of time-series data;
      calculating a first mean diversity value for the fourth set of time-series data;
      determining a Firmicutes to Bacteroidetes ratio (F/B ratio) of the second set of time-series data;
      determining a first harmonic mean of the F/B ratio;
      calculating a first IgG subclass ratio for the second set of time-series data at least by:
         determining a relative concentration of immunoglobulin G (IgG) subclass in the second set of time-series data;
      generating a statistical classifier model at least by:
         obtaining a set of training data corresponding to health data for a plurality of patients, the health data comprising:
            at least one input variable corresponding to: a particular mean diversity value, a particular harmonic mean of a F/B ratio, and a particular ratio of IgG2/IgG; and
            a label indicating a presence of an Irritable Bowel Syndrome (IBS) condition;
         iteratively performing a logistic regression operation on the set of training data to train the statistical classifier model to generate a statistical significance value representing a statistical significance of a microbiota change and an IgG subclass relative concentration change;
      applying the statistical classifier model to an input data set comprising: the first mean diversity value, the first harmonic mean of the F/B ratio, and the first IgG subclass ratio of IgG2 to IgG;
      responsive to applying the statistical classifier model to the input data set: generating, by the statistical classifier model, a first statistical significance value based on the first mean diversity value, the first harmonic mean of the F/B ratio, and the first IgG subclass ratio; and
      based on the first statistical significance value, determining a diagnosis of IBS conditions in the patient.

2. The system of claim 1, wherein the operations further comprise:
   initiating an intervening action based on the diagnosis of IBS conditions in the patient,
   wherein the intervening action comprises at least one of:
      issuing a notification to a caregiver associated with the patient;
      automatically scheduling healthcare resources for treating the patient; or
      modifying a computer program associated with a care plan for the patient.

3. The system of claim 1 further comprising, determining genera counts with phylum-level mappings from the first series of specimens, wherein the genera counts with phylum-level mappings correspond to the first set of time-series data.

4. The system of claim 3, wherein the determining the genera counts with phylum-level mappings comprises determining and totalizing rarefied relative abundances of genera in the phylum Firmicutes, and determining and totalizing rarefied relative abundances of genera in the phylum Bacteroidetes in each measurement of the first set of time-series data.

5. The system of claim 1 further comprising, based on a statistical significance value, determining a likelihood of a patient's IBS condition being responsive to a particular treatment.

6. The system of claim 5, wherein the treatment comprises administering eluxadoline, alosetron, or rifaxmin.

7. The system of claim 1, wherein determining the diagnosis of IBS comprises determining a likelihood of a presence or absence of IBS based on the statistical significance value.

8. The system of claim 1, wherein a diversity value of the fourth set of time-series data comprises an alpha diversity, and wherein the first mean diversity value comprises a value representing a mean alpha diversity.

9. The system of claim 8, wherein the mean alpha diversity is determined as the arithmetic mean of diversity values of the microbiota-related time series measurements.

10. The system of claim 1 further comprising assembling a phylogenetic tree matrix with a distance metric for the taxa represented in the first set of time series data.

11. The system of claim 10, wherein a Kimura 2-parameter (K80) model is utilized and the phylogenetic tree matrix is determined by Unweighted Pair Group Method with Arithmetic Mean (UPGMA) methods on the K80 distance matrix, for the taxa represented in the first set of time series data.

12. The system of claim 1, wherein the second series of specimens comprise serum specimens of immunoglobulin G, wherein the IgG subclass comprises IgG2, and wherein the relative concentration of IgG subclass is determined as a fraction of IgG2 to total serum IgG.

13. The system of claim 1, further comprising determining a composite variable from the first harmonic mean of the F/B ratio and the first mean diversity value, as a ratio of the F/B ratio harmonic mean to the mean diversity.

14. A computerized diagnostic method for determining a prognosis of IBS in a subject suffering from a functional gastrointestinal condition, the method comprising:

acquiring at least three serial specimens from the subject, the specimens including serum;

generating a set of time-series data comprising measurements from the specimens, wherein the measurements represent abundances of microbial taxa;

from the specimens, determining an IgG2 subclass concentration as a fraction of a total serum IgG;

calculating a first IgG subclass ratio for the at least three serial specimens at least by:

determining a relative concentration of IgG to IgG2 in the at least three serial specimens;

obtaining treatment metadata for a health condition of interest, the treatment metadata associated with the set of time-series data;

performing rarefaction on taxa abundances of each specimen to normalize taxon counts to a standard count to generate rarefied abundances for the at least three serial specimens;

calculating microbiota diversity of each specimen;

determining a Firmicutes/Bacteroidetes (F/B) ratio value for each of the rarefied abundances;

determining a first harmonic mean of the F/B ratio values;

determining a microbiota diversity value for each of the at least three serial specimens;

determining a first arithmetic mean of the diversity values;

generating a statistical classifier model at least by:

obtaining a set of training data corresponding to health data for a plurality of patients, the health data comprising:

at least one input variable corresponding to: a particular mean diversity value, a particular harmonic mean of a F/B ratio, and a particular ratio of IgG2/IgG; and a label indicating a presence of a gastrointestinal condition;

iteratively performing a logistic regression operation on the set of training data to train the statistical classifier model to generate a statistical significance value representing a statistical significance of a microbiota change and an IgG subclass relative concentration change;

applying the statistical classifier model to an input data set comprising:

the first arithmetic mean of the diversity values, the first harmonic mean of the F/B ratio, and the first IgG subclass ratio, responsive to applying the statistical classification model to the input data set: generating, by the statistical classifier model, a first statistical significance value based on the first mean diversity value, the first harmonic mean of the F/B ratio, and the first IgG subclass ratio;

based on the first statistical significance value, determining a diagnosis representing a likelihood of the presence of the functional gastrointestinal condition.

15. The method of claim 14 further comprising: determining a likely effectiveness of a medical treatment that is directed to a microbiota profile, microbiota diversity, or an immune response in the subject based on the statistical significance.

16. The method of claim 14, further comprising:

obtaining the measurements representing the abundances of microbial taxa at least by applying a 16S rRNA sequencing method including amplification, depending on the total count of organisms in the specimens and an efficiency of nucleotide extraction, and the measurements in machine-readable persistent storage.

17. The method of claim 14, further comprising:

determining operational taxonomic units (OTUs) in each specimen by pyrosequencing of 16S microbial rRNA.

18. The method of claim 14, wherein a phylogenetic tree matrix with distance metric is determined so as to enable determination of phylogenetic-distance-based diversity metrics, where the tree matrix is calculated preferably by UPGMA methods on the K80 distance matrix.

19. The method of claim 14, further comprising:

electronically transmitting an advisory message regarding the diagnosis to a caregiver associated with the subject.

20. The method of claim 14, wherein a treatment is administered to the patient based at least in part on the diagnosis of the IBS conditions in the patient.

21. The method of claim 20, wherein administering the treatment comprises generating a recommendation to modify an administration of a treatment procedure for the patient.

22. The method of claim 21, wherein administering the treatment comprises modifying an administration of a treatment procedure for the patient.

* * * * *